United States Patent
Ng et al.

(10) Patent No.: US 10,939,488 B2
(45) Date of Patent: Mar. 2, 2021

(54) METHOD AND SYSTEM FOR CONTROLLING COMMUNICATION BETWEEN DEVICES OF A WIRELESS BODY AREA NETWORK FOR AN MEDICAL DEVICE SYSTEM

(71) Applicant: MEDTRONIC MINIMED, INC., Northridge, CA (US)

(72) Inventors: Anthony C. Ng, Calabasas, CA (US); Yazid E. Ould Sidi, Northridge, CA (US)

(73) Assignee: Medtronic MiniMed, Inc., Northridge, CA (US)

(*) Notice: Subject to any disclaimer, the term of this patent is extended or adjusted under 35 U.S.C. 154(b) by 0 days.

(21) Appl. No.: 16/417,487

(22) Filed: May 20, 2019

(65) Prior Publication Data
US 2020/0374952 A1 Nov. 26, 2020

(51) Int. Cl.
| | |
|---|---|
| *H04W 76/14* | (2018.01) |
| *A61M 5/172* | (2006.01) |
| *H04W 84/18* | (2009.01) |
| *H04W 76/18* | (2018.01) |

(52) U.S. Cl.
CPC .......... *H04W 76/14* (2018.02); *A61M 5/1723* (2013.01); *A61M 2205/3553* (2013.01); *A61M 2205/3561* (2013.01); *A61M 2205/3584* (2013.01); *A61M 2205/3592* (2013.01); *A61M 2205/50* (2013.01); *A61M 2230/201* (2013.01); *H04W 76/18* (2018.02); *H04W 84/18* (2013.01)

(58) Field of Classification Search
CPC ... H04W 76/14; H04W 28/06; A61M 5/1723; G06F 19/3418; H04L 69/08; H04L 67/12
See application file for complete search history.

(56) References Cited

U.S. PATENT DOCUMENTS

| | | |
|---|---|---|
| 4,562,751 A | 1/1986 | Nason et al. |
| 4,685,903 A | 8/1987 | Cable et al. |
| 4,755,173 A | 7/1988 | Konopka et al. |
| 5,080,653 A | 1/1992 | Voss et al. |
| 5,097,122 A | 3/1992 | Colman et al. |
| 5,391,250 A | 2/1995 | Cheney, II et al. |
| 5,485,408 A | 1/1996 | Blomquist |
| 5,505,709 A | 4/1996 | Funderburk et al. |
| 5,522,803 A | 6/1996 | Teissen-Simony |

(Continued)

*Primary Examiner* — Wei Zhao
(74) *Attorney, Agent, or Firm* — Lorenz & Kopf, LLP

(57) ABSTRACT

A method and system are provided for controlling which communication interface of a plurality of communication interfaces is used for communication between a plurality of devices that can be part of a wireless body area network for a medical device system. The communication interfaces can include a body area network communication interface and a far field communication interface. A controller can determine whether a first device is able to establish a communication link with a second device that is located in a coverage region of the wireless body area network using a first body area network communication interface. If so, the controller can determine whether a quality of service over the communication link is greater than or equal to a first threshold, and if so, the first body area network communication interface can be used to communicate data from the first device to the second device via magnetic signals.

20 Claims, 10 Drawing Sheets

(56) References Cited

U.S. PATENT DOCUMENTS

| | | |
|---|---|---|
| 5,665,065 A | 9/1997 | Colman et al. |
| 5,800,420 A | 9/1998 | Gross et al. |
| 5,807,375 A | 9/1998 | Gross et al. |
| 5,925,021 A | 7/1999 | Castellano et al. |
| 5,954,643 A | 9/1999 | Van Antwerp et al. |
| 6,017,328 A | 1/2000 | Fischell et al. |
| 6,088,608 A | 7/2000 | Schulman et al. |
| 6,119,028 A | 9/2000 | Schulman et al. |
| 6,186,982 B1 | 2/2001 | Gross et al. |
| 6,246,992 B1 | 6/2001 | Brown |
| 6,248,067 B1 | 6/2001 | Causey, III et al. |
| 6,248,093 B1 | 6/2001 | Moberg |
| 6,355,021 B1 | 3/2002 | Nielsen et al. |
| 6,379,301 B1 | 4/2002 | Worthington et al. |
| 6,485,465 B2 | 11/2002 | Moberg et al. |
| 6,544,212 B2 | 4/2003 | Galley et al. |
| 6,554,798 B1 | 4/2003 | Mann et al. |
| 6,558,320 B1 | 5/2003 | Causey, III et al. |
| 6,558,351 B1 | 5/2003 | Steil et al. |
| 6,589,229 B1 | 7/2003 | Connelly et al. |
| 6,591,876 B2 | 7/2003 | Safabash |
| 6,641,533 B2 | 11/2003 | Causey, III et al. |
| 6,659,980 B2 | 12/2003 | Moberg et al. |
| 6,736,797 B1 | 5/2004 | Larsen et al. |
| 6,740,072 B2 | 5/2004 | Starkweather et al. |
| 6,749,587 B2 | 6/2004 | Flaherty |
| 6,752,787 B1 | 6/2004 | Causey, III et al. |
| 6,766,183 B2 | 7/2004 | Walsh et al. |
| 6,801,420 B2 | 10/2004 | Talbot et al. |
| 6,804,544 B2 | 10/2004 | Van Antwerp et al. |
| 6,817,990 B2 | 11/2004 | Yap et al. |
| 6,827,702 B2 | 12/2004 | Lebel et al. |
| 6,932,584 B2 | 8/2005 | Gray et al. |
| 7,003,336 B2 | 2/2006 | Holker et al. |
| 7,029,444 B2 | 4/2006 | Shin et al. |
| 7,066,909 B1 | 6/2006 | Peter et al. |
| 7,137,964 B2 | 11/2006 | Flaherty |
| 7,303,549 B2 | 12/2007 | Flaherty et al. |
| 7,323,142 B2 | 1/2008 | Pendo et al. |
| 7,399,277 B2 | 7/2008 | Saidara et al. |
| 7,402,153 B2 | 7/2008 | Steil et al. |
| 7,442,186 B2 | 10/2008 | Blomquist |
| 7,602,310 B2 | 10/2009 | Mann et al. |
| 7,621,893 B2 | 11/2009 | Moberg et al. |
| 7,647,237 B2 | 1/2010 | Malave et al. |
| 7,699,807 B2 | 4/2010 | Faust et al. |
| 7,727,148 B2 | 6/2010 | Talbot et al. |
| 7,785,313 B2 | 8/2010 | Mastrototaro |
| 7,806,886 B2 | 10/2010 | Kanderian, Jr. et al. |
| 7,819,843 B2 | 10/2010 | Mann et al. |
| 7,828,764 B2 | 11/2010 | Moberg et al. |
| 7,879,010 B2 | 2/2011 | Nunn et al. |
| 7,890,295 B2 | 2/2011 | Shin et al. |
| 7,892,206 B2 | 2/2011 | Moberg et al. |
| 7,892,748 B2 | 2/2011 | Norrild et al. |
| 7,901,394 B2 | 3/2011 | Ireland et al. |
| 7,942,844 B2 | 5/2011 | Moberg et al. |
| 7,946,985 B2 | 5/2011 | Mastrototaro et al. |
| 7,955,305 B2 | 6/2011 | Moberg et al. |
| 7,963,954 B2 | 6/2011 | Kavazov |
| 7,977,112 B2 | 7/2011 | Burke et al. |
| 7,979,259 B2 | 7/2011 | Brown |
| 7,985,330 B2 | 7/2011 | Wang et al. |
| 8,024,201 B2 | 9/2011 | Brown |
| 8,100,852 B2 | 1/2012 | Moberg et al. |
| 8,114,268 B2 | 2/2012 | Wang et al. |
| 8,114,269 B2 | 2/2012 | Cooper et al. |
| 8,137,314 B2 | 3/2012 | Mounce et al. |
| 8,181,849 B2 | 5/2012 | Bazargan et al. |
| 8,182,462 B2 | 5/2012 | Istoc et al. |
| 8,192,395 B2 | 6/2012 | Estes et al. |
| 8,195,265 B2 | 6/2012 | Goode, Jr. et al. |
| 8,202,250 B2 | 6/2012 | Stutz, Jr. |
| 8,207,859 B2 | 6/2012 | Enegren et al. |
| 8,226,615 B2 | 7/2012 | Bikovsky |
| 8,257,259 B2 | 9/2012 | Brauker et al. |
| 8,267,921 B2 | 9/2012 | Yodfat et al. |
| 8,275,437 B2 | 9/2012 | Brauker et al. |
| 8,277,415 B2 | 10/2012 | Mounce et al. |
| 8,292,849 B2 | 10/2012 | Bobroff et al. |
| 8,298,172 B2 | 10/2012 | Nielsen et al. |
| 8,303,572 B2 | 11/2012 | Adair et al. |
| 8,305,580 B2 | 11/2012 | Aasmul |
| 8,308,679 B2 | 11/2012 | Hanson et al. |
| 8,313,433 B2 | 11/2012 | Cohen et al. |
| 8,318,443 B2 | 11/2012 | Norrild et al. |
| 8,323,250 B2 | 12/2012 | Chong et al. |
| 8,343,092 B2 | 1/2013 | Rush et al. |
| 8,352,011 B2 | 1/2013 | Van Antwerp et al. |
| 8,353,829 B2 | 1/2013 | Say et al. |
| 8,474,332 B2 | 7/2013 | Bente, IV |
| 8,674,288 B2 | 3/2014 | Hanson et al. |
| 8,780,835 B2 * | 7/2014 | Hakola ............... H04W 74/008 370/245 |
| 9,226,290 B2 * | 12/2015 | Gaal ............... H04W 72/0446 |
| 2007/0123819 A1 | 5/2007 | Mernoe et al. |
| 2010/0160861 A1 | 6/2010 | Causey, III et al. |
| 2014/0066889 A1 | 3/2014 | Grosman et al. |
| 2017/0300654 A1 * | 10/2017 | Stein ............... H01Q 1/1214 |

\* cited by examiner

| STANDARD | NMFI | NFC | BLUETOOTH | BLE |
|---|---|---|---|---|
| FREQUENCY [MHz] | 10.6 | 13.56 | 2400 | 2400 |
| DATA RATE [kbps] | 596 | 106 ~ 848 | 2000 ~ 3000 | 1000 ~ 2000 |
| RANGE | UP TO 3 m | 10 cm OR LESS | 100 m OR MORE | 50 m OR LESS |

TABLE 1

*FIG. 6*

METHOD AND SYSTEM FOR CONTROLLING COMMUNICATION BETWEEN DEVICES OF A WIRELESS BODY AREA NETWORK FOR AN MEDICAL DEVICE SYSTEM

TECHNICAL FIELD

Embodiments of the subject matter described herein relate generally to medical devices and medical device systems and, more specifically, to a method and system for controlling communication devices that can be part of a wireless body area network for a medical device system, such as an insulin infusion system.

BACKGROUND

Wireless devices, such as cellular telephones, mobile computers, personal digital assistants, digital media players, portable video game devices, and the like, and related wireless communication techniques and protocols have become ubiquitous in modern society. More recently, portable medical devices having wireless data communication capabilities are becoming increasingly popular, especially for patients that have conditions that must be monitored on a continuous or frequent basis. For example, diabetics are usually required to modify and monitor their daily lifestyle to keep their body in balance, in particular, their blood glucose ("BG") levels. Individuals with Type 1 diabetes and some individuals with Type 2 diabetes use insulin to control their BG levels. To do so, diabetics routinely keep strict schedules, including ingesting timely nutritious meals, partaking in exercise, monitoring BG levels daily, and adjusting and administering insulin dosages accordingly. Diabetics may utilize wireless medical devices that are deployed in a network environment in a manner that facilitates data communication between two or more separate devices.

A number of insulin pump systems are designed to deliver accurate and measured doses of insulin via infusion sets (an infusion set delivers the insulin through a small diameter tube that terminates at a cannula inserted under the patient's skin). In lieu of a syringe, the patient can simply activate the insulin pump to administer an insulin bolus as needed, for example, in response to the patient's current BG level. A patient can measure his BG level using a BG measurement device, such as a test strip meter, a continuous glucose measurement system, or the like. BG measurement devices use various methods to measure the BG level of a patient, such as a sample of the patient's blood, a sensor in contact with a bodily fluid, an optical sensor, an enzymatic sensor, or a fluorescent sensor. When the BG measurement device has generated a BG measurement, the measurement is displayed on the BG measurement device. A continuous glucose monitoring system can monitor the patient's sensor glucose (SG) level (e.g., subcutaneous tissue glucose level) in real-time. This allows delivery of insulin to be calculated in real-time with dosage calculated in a software algorithm based on measured sensor glucose level, or a closed-loop algorithm.

Insulin pumps and continuous glucose monitoring devices that are part of an insulin infusion system may also be configured to communicate with remote control devices, monitoring or display devices, BG meters, and other devices associated with such an infusion system. For example, a continuous glucose monitoring sensor may include or cooperate with a wireless radio frequency ("RF") transmitter that communicates with a BG monitor device or feature within the infusion system. As another example, the infusion system may include a handheld remote control that communicates with the infusion pump device using wireless communication technologies such as classical Bluetooth® (BT) or Bluetooth Low Energy® (BLE) technologies.

The insulin pump, continuous glucose monitoring (CGM) device, and other devices, such as a smart phone and a Blood Glucose Monitor (BGM), can be different parts of an insulin infusion system. The communication technologies described above can greatly simplify communication among the various devices that are part of an insulin infusion system. Collectively these devices can form a wireless body area network that can be used, for example, to exchange monitor and therapy (control) data among multiple medical devices that are either worn on or near a patient's body. For instance, therapy data such as measured glucose values (SG values) and therapy settings (parameters for bolus delivery) can be transferred wirelessly among devices within the body area network.

Accordingly, it is desirable to provide a wireless body area network that employs communications technologies that are effective in a wide variety of operating environments to allow communication among devices that are part of an insulin infusion system. It would also be desirable if these communications technologies are secure and power efficient. Furthermore, other desirable features and characteristics will become apparent from the subsequent detailed description and the appended claims, taken in conjunction with the accompanying drawings and the foregoing technical field and background.

BRIEF SUMMARY

In one embodiment, a method is provided for controlling which communication interface of a plurality of communication interfaces is used for communication between a plurality of devices that can be part of a wireless body area network for a medical device system depending on their respective locations with respect to a first device. The plurality of communication interfaces can include a body area network communication interface and a far field communication interface. A controller can determine whether the first device is able to establish a communication link with a second device that is located in a coverage region of the wireless body area network using a first body area network communication interface. In one embodiment, the medical device system is an insulin infusion system that includes an insulin infusion device configured to deliver insulin to a user, and the first device and the second device can each be one of, for example, a mobile client device, a glucose sensor arrangement, or the insulin infusion device.

When the controller determines that the first device is able to establish a communication link with the second device using the first body area network communication interface, the controller can determine whether a quality of service over the communication link is greater than or equal to a first threshold, and when the controller determines that the quality of service over the communication link is greater than or equal to the first threshold, the first body area network communication interface can be used to communicate data from the first device to the second device via magnetic signals.

In one embodiment, the first device and the second device can each include a plurality of body area network communication interfaces that are used to communicate via near-field communications using magnetic signals. For example, in one implementation, the first body area network communication interface can be a near-field magnetic induction (NFMI) radio communication interface; a near-field electromagnetic induction (NFeMI) radio communication interface; a near-field communication (NFC) interface; or a high-frequency radio-frequency identification (RFID) communication interface. In addition, the first device and the second device may also each comprise a plurality of far-field communication interfaces that are used to communicate via far-field communications using electromagnetic signals. As such, the first far-field communication interface can be, for example, a Bluetooth Low Energy® (BLE) communication interface; a classical Bluetooth® (BT) communication interface; or a Wireless Local Area Network (WLAN) communication interface.

When the controller determines that the first device is unable to establish a communication link with the second device using the first body area network communication interface or that the quality of service over the communication link is less than the first threshold, the controller can determine whether there is a second body area network communication interface available to potentially use to communicate with the second device, and if so, the controller can determine whether the first device is able to establish a communication link with the second device that is located in the coverage region of the wireless body area network using the second body area network communication interface. When the controller determines that the first device is able to establish the communication link with the second device using the second body area network communication interface, the controller can determine whether the quality of service over that communication link is greater than or equal to the first threshold, and if so, can use the second body area network communication interface to communicate the data from the first device to the second device via magnetic signals.

In one embodiment, when the controller determines that the second body area network communication interface is not available, the controller can select a first far-field communication interface, and then determine whether the first device is able to establish a communication link with the second device using the first far-field communication interface, and if so, can then determine whether the quality of service over that communication link is greater than or equal to the first threshold. In one embodiment, when the controller determines that the quality of service over the communication link is greater than or equal to the first threshold, the controller can use the first far-field communication interface to communicate the data from the first device to the second device via electromagnetic signals. In another embodiment, when the controller determines that the quality of service over the communication link is greater than or equal to the first threshold, the controller can determine whether data to be communicated by the first device is secure data, and use the first far-field communication interface to communicate the data from the first device to the second device (via electromagnetic signals) when the controller determines that the data to be communicated by the first device is not secure data. If the data is determined to be secure data, then the controller can wait for one of the body area network communication interfaces to become available and be able to establish a communication link with the second device meet a quality of service over that communication link before communicating the secure data from the first device to the second device (via magnetic signals) using that body area network communication interface.

In another embodiment, when the controller determines that the first device is unable to establish a communication link with the second device using the first far-field communication interface or that the quality of service over the communication link established with the second device using the first far-field communication interface is less than the first threshold, the controller can determine whether there are any additional far-field communication interfaces that are available to potentially use to communicate with the second device, and if so select a second far-field communication interface and then determine whether the first device is able to establish a communication link with the second device using the second far-field communication interface. If so, the controller can determine whether the quality of service over that communication link is greater than or equal to the first threshold, and if so, determine whether data to be communicated by the first device is secure data. When the controller determines that the quality of service over that communication link is greater than or equal to the first threshold, and the data to be communicated by the first device is not secure data, the controller can use the second far-field communication interface to communicate the data from the first device to the second device via electromagnetic signals.

In another embodiment, a first device is provided that comprises at least one processor device, and a non-transitory processor-readable medium operatively associated with the at least one processor device. The processor-readable medium comprises executable instructions configurable to cause the at least one processor device to perform a method for controlling which communication interface of a plurality of communication interfaces is used for communication with a second device that can be part of a wireless body area network for a medical device system, where the first device and the second device are implemented as part of the medical device system. The plurality of communication interfaces can include a body area network communication interface and a far field communication interface. In one embodiment, the first device and the second device are each exclusively one of: a mobile client device; an insulin infusion device configured to deliver insulin to a user; and a glucose sensor arrangement.

In one embodiment, the first device and the second device each comprise: a plurality of body area network communication interfaces that are used to communicate via near-field communications using magnetic signals, and a plurality of far-field communication interfaces that are used to communicate via far-field communications using electromagnetic signals. In one implementation, the body area network communication interfaces can include a near-field magnetic induction (NFMI) radio communication interface; a near-field electromagnetic induction (NFeMI) radio communication interface; a near-field communication (NFC) interface; or a high-frequency radio-frequency identification (RFID) communication interface; and the far-field communication interfaces can include a Bluetooth Low Energy® (BLE) communication interface; a classical Bluetooth® (BT) communication interface; or a Wireless Local Area Network (WLAN) communication interface.

In one embodiment, the method for controlling which communication interface of the plurality of communication interfaces is used for communication with the second device can include: determining whether the first device is able to establish a communication link with a second device that is located in a coverage region of the wireless body area network using a first body area network communication interface, wherein the first device and the second device are implemented as part of the medical device system; when the first device is determined to be able to establish a communication link with the second device using the first body area network communication interface: determining whether a quality of service over the communication link is greater than or equal to a first threshold; and using the first body area network communication interface to communicate data from the first device to the second device via magnetic signals when the quality of service over the communication link is determined to be greater than or equal to the first threshold.

In one embodiment, when the first device is unable to establish a communication link with the second device using the first body area network communication interface or when the quality of service over the communication link is less than the first threshold, the method can further include determining whether a second body area network communication interface is available to potentially use to communicate with the second device. When the second body area network communication interface is determined to be available, the method can further include determining whether the first device is able to establish a communication link with the second device that is located in the coverage region of the wireless body area network using the second body area network communication interface; determining, when the first device is determined to be able to establish the communication link with the second device using the second body area network communication interface, whether the quality of service over that communication link is greater than or equal to the first threshold; and using the second body area network communication interface to communicate the data from the first device to the second device via magnetic signals when the quality of service over that communication link is greater than or equal to the first threshold.

In one embodiment, when the second body area network communication interface is determined to be not available, the method can further include selecting a first far-field communication interface; and determining whether the first device is able to establish a communication link with the second device that is located in the coverage region of the wireless body area network using the first far-field communication interface. When the first device is determined to be able to establish the communication link with the second device using the first far-field communication interface, the method can further include determining whether the quality of service over that communication link is greater than or equal to the first threshold; determining, when the quality of service over that communication link is determined to be greater than or equal to the first threshold, whether data to be communicated by the first device is secure data; using the first far-field communication interface to communicate the data from the first device to the second device via electromagnetic signals when the data to be communicated by the first device is determined not to be secure data; and waiting for a body area network communication interface to become available when the data to be communicated by the first device is secure data.

In another embodiment, a wireless body area network for an insulin infusion system is provided. The wireless body area network can include a plurality of devices that can be part of the wireless body area network depending on their respective locations with respect to a first device. The devices can include an insulin infusion device configured to deliver insulin to a user; a glucose sensor; and a mobile client device. One of the plurality of devices can be referred to as the first device and another one of the plurality of devices can be referred to as a second device. The first device can include a processor device that controls communication with the other devices that can be part of the wireless body area network depending on their respective locations with respect to the first device, and a non-transitory processor-readable medium operatively associated with the processor device. The processor-readable medium comprises executable instructions configurable to cause the processor device to perform a method for controlling which communication interface of a plurality of communication interfaces is to be used for communication with the second device. The plurality of communication interfaces can include a body area network communication interface and a far field communication interface. In one embodiment, the first device and the second device each can each include a plurality of body area network communication interfaces that are used to communicate via near-field communications using magnetic signals, and a plurality of far-field communication interfaces that are used to communicate via far-field communications using electromagnetic signals. For example, the body area network communication interfaces can include: a near-field magnetic induction (NFMI) radio communication interface; a near-field electromagnetic induction (NFeMI) radio communication interface; a near-field communication (NFC) interface; or a high-frequency radio-frequency identification (RFID) communication interface, and the far-field communication interfaces can include: a Bluetooth Low Energy® (BLE) communication interface; a classical Bluetooth® (BT) communication interface; or a Wireless Local Area Network (WLAN) communication interface.

The method can include determining whether the first device is able to establish a communication link with a second device that is located in a coverage region of the wireless body area network using a first body area network communication interface; when the first device is determined to be able to establish a communication link with the second device using the first body area network communication interface: determining whether a quality of service over the communication link is greater than or equal to a first threshold by comparing at least one link quality metric to the first threshold to determine whether the quality of service over that communication link is adequate; and using the first body area network communication interface to communicate data from the first device to the second device via magnetic signals when the quality of service over the communication link is determined to be greater than or equal to the first threshold.

When the first device is unable to establish a communication link with the second device using the first body area network communication interface or when the quality of service over the communication link is less than the first threshold, the method can include determining whether a second body area network communication interface is available to potentially use to communicate with the second device, and when the second body area network communication interface is determined to be available: determining whether the first device is able to establish a communication link with the second device that is located in the coverage region of the wireless body area network using the second body area network communication interface.

When the first device is determined to be able to establish the communication link with the second device using the second body area network communication interface, the method can further include determining whether the quality of service over that communication link is greater than or equal to the first threshold, and when the quality of service over that communication link is greater than or equal to the first threshold, using the second body area network communication interface to communicate the data from the first device to the second device via magnetic signals.

In one embodiment, when the second body area network communication interface is determined to be not available, the method can further include selecting a first far-field communication interface, and determining whether the first device is able to establish a communication link with the second device using the first far-field communication interface. When the first device is determined to be able to establish the communication link with the second device using the first far-field communication interface, the method can further include determining whether the quality of service over that communication link is greater than or equal to the first threshold, and when the quality of service over that communication link is determined to be greater than or equal to the first threshold, determining whether data to be communicated by the first device is secure data. When the data to be communicated by the first device is determined not to be secure data, the method can further include using the first far-field communication interface to communicate the data from the first device to the second device via electromagnetic signals. By contrast, when the data to be communicated by the first device is secure data, the method can further include waiting for a body area network communication interface to become available.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures.

FIG. 6 is a table that shows characteristics of various communication standards in accordance with one non-limiting implementation;

DETAILED DESCRIPTION

Figure 1:
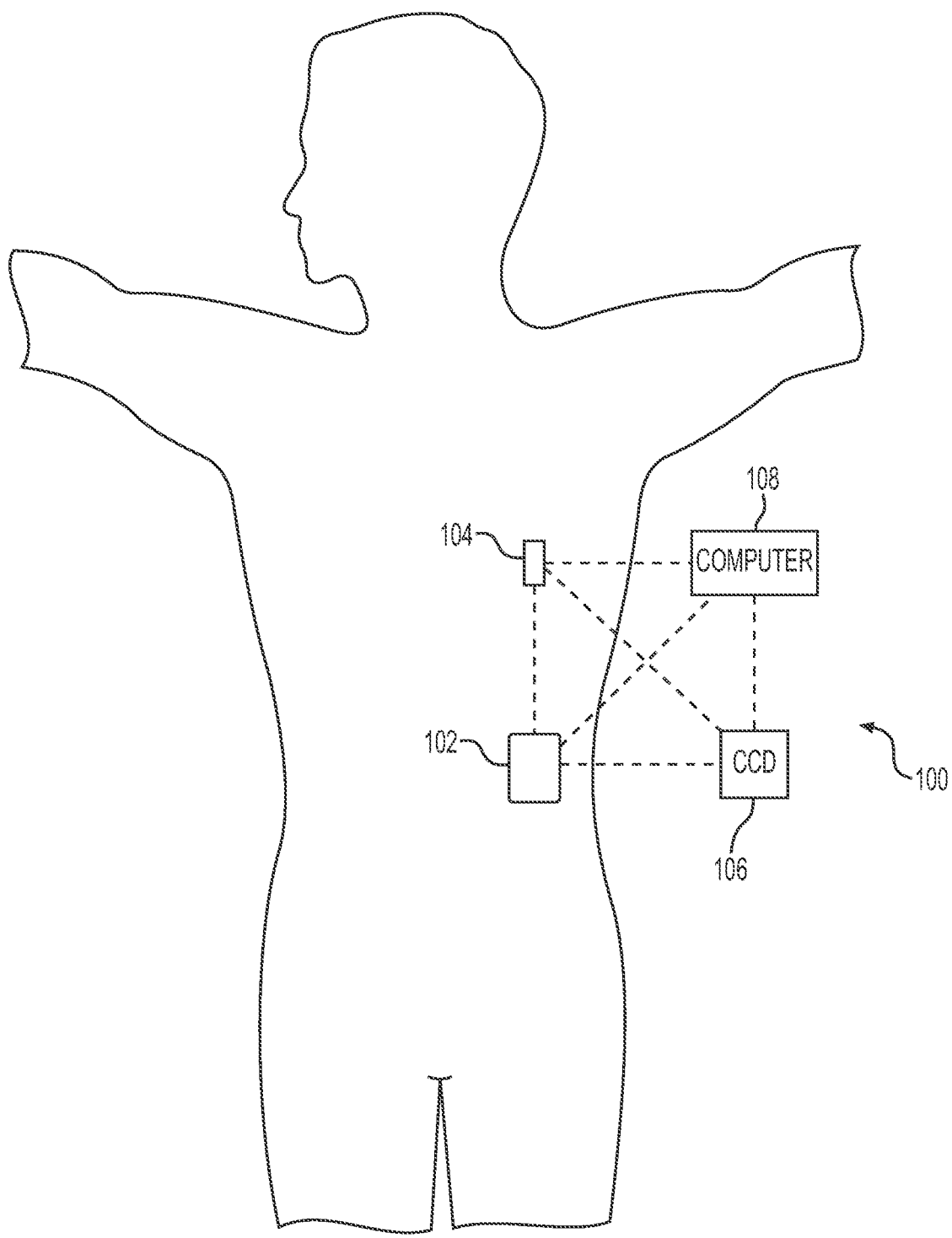
FIG. 1 depicts an exemplary embodiment of an infusion system.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

Techniques and technologies may be described herein in terms of functional and/or logical block components, and with reference to symbolic representations of operations, processing tasks, and functions that may be performed by various computing components or devices. Such operations, tasks, and functions are sometimes referred to as being computer-executed, computerized, software-implemented, or computer-implemented. It should be appreciated that the various block components shown in the figures may be realized by any number of hardware, software, and/or firmware components configured to perform the specified functions. For example, an embodiment of a system or a component may employ various integrated circuit components, e.g., memory elements, digital signal processing elements, logic elements, look-up tables, or the like, which may carry out a variety of functions under the control of one or more microprocessors or other control devices.

When implemented in software, firmware, or processor-readable instructions, various elements of the systems described herein are essentially the code segments or instructions that perform the various tasks. In certain embodiments, the program or code segments are stored in a tangible processor-readable medium, which may include any medium that can store or transfer information. Examples of a non-transitory and processor-readable medium include an electronic circuit, a semiconductor memory device, a ROM, a flash memory, an erasable ROM (EROM), a floppy diskette, a CD-ROM, an optical disk, a hard disk, or the like.

Exemplary embodiments of the subject matter described herein are implemented in conjunction with medical devices, such as portable electronic medical devices. Although many different applications are possible, the following description focuses on embodiments that incorporate an insulin infusion device (or insulin pump) as part of an infusion system deployment. For the sake of brevity, conventional techniques related to infusion system operation, insulin pump and/or infusion set operation, and other functional aspects of the systems (and the individual operating components of the systems) may not be described in detail here. Examples of infusion pumps may be of the type described in, but not limited to, U.S. Pat. Nos. 4,562,751; 4,685,903; 5,080,653; 5,505,709; 5,097,122; 6,485,465; 6,554,798; 6,558,320; 6,558,351; 6,641,533; 6,659,980; 6,752,787; 6,817,990; 6,932,584; and 7,621,893; each of which are herein incorporated by reference.

Generally, a fluid infusion device includes a motor or other actuation arrangement that is operable to linearly displace a plunger (or stopper) of a fluid reservoir provided within the fluid infusion device to deliver a dosage of fluid, such as insulin, to the body of a user. Dosage commands that govern operation of the motor may be generated in an automated manner in accordance with the delivery control scheme associated with a particular operating mode, and the dosage commands may be generated in a manner that is influenced by a current (or most recent) measurement of a physiological condition in the body of the user. For example, in a closed-loop or automatic operating mode, dosage commands may be generated based on a difference between a current (or most recent) measurement of the interstitial fluid glucose level in the body of the user and a target (or reference) glucose setpoint value. In this regard, the rate of infusion may vary as the difference between a current measurement value and the target measurement value fluctuates. For purposes of explanation, the subject matter is described herein in the context of the infused fluid being insulin for regulating a glucose level of a user (or patient); however, it should be appreciated that many other fluids may be administered through infusion, and the subject matter described herein is not necessarily limited to use with insulin.

While the communication methods described in the background section above can greatly simplify communication among the various devices that are part of a medical device system, such as an insulin infusion system, there are certain drawbacks associated with these communication technologies. For example, in some scenarios, a wearable or implantable devices, such as the insulin pump, may be located on the opposite side of the patient's body as other devices, such as a glucose sensing arrangement, a BG meter, the patient's smartphone, etc. When two of the devices are located on opposite sides of the patient's body they may be unable to communicate through the patient's body because the human body is made up primarily of "salt water," which is an effective absorber of RF energy. For example, when devices that are part of an medical device system, such as an insulin infusion system, utilize Bluetooth Low Energy® (BLE) technology to communicate, the BLE® communication interface can operate at 2.4 GHz, and electromagnetic energy penetrates no more than 2 centimeters into the outer tissues of the human body. Thus, using BLE® to communicate directly across the human body (or through water) is simply not possible when devices, such as an insulin pump and a CGM, are worn across the body without direct line-of-sight and reflection of adjacent objects. This effect is more severe at higher radio frequencies. Transmission problems can also occur when the patient is in water (e.g., swimming, bathing, showering, etc.) because water absorbs RF energy. A similar issue can occur when the patient is sleeping in certain positions because there may be no direct communication path between the devices due to blockage by the human body. In addition, problems can also arise, for example, when the patient is in open areas.

To address this issue, in one implementation, methods, systems and apparatus are provided for controlling communication among devices that can be part of a wireless body area network for a medical device system, namely, an insulin infusion system. In accordance with certain embodiments, the insulin infusion system includes an insulin infusion device configured to deliver insulin to a user, a mobile client device like a smartphone, a glucose sensor arrangement, a blood glucose meter, etc. Each device can include a controller that can dynamically switch a radio frequency (RF) topology scheme that is used to communicate data to other devices depending on factors such as the proximity of a device to one or more other devices that are part of the wireless body area network, the quality of service of the communication link between devices, and the security type of the data that is being communicated between devices.

In one embodiment, the controller can attempt to establish a communication link with one or more other devices (e.g., that may be located in a coverage region of the wireless body area network) using a body area network communication interface (e.g., a near-field magnetic induction (NFMI) radio communication interface (also referred to herein as a NFMI radio communication interface); a near-field electromagnetic induction (NFeMI) radio communication interface; a near-field communication (NFC) interface; a high-frequency radio-frequency identification (RFID) communication interface, etc.). When a communication link is able to be established using one of the body area network communication interfaces, the controller can determine whether a quality of service over the communication link is greater than or equal to a threshold (e.g., by comparing one or more link quality metrics to the corresponding threshold(s) to determine whether the quality of service over that communication link is adequate). If so, the controller can route data to that body area network communication interface for communication to the other device(s) using magnetic signals.

When the controller determines that a communication link cannot be established using one of the body area network communication interfaces or that the quality of service over any communication links that can be established are less than the threshold, the controller can attempt to establish a communication link with the other device(s) using a far-field communication interface (e.g., a Bluetooth Low Energy® (BLE®) communication interface; a classical Bluetooth® (BT) communication interface; a Wireless Local Area Network (WLAN) communication interface, etc.). If so, the controller can then determine whether the quality of service over that established communication link is greater than or equal to the threshold, and if so can use that far-field communication interface to communicate the data to the other device(s) using electromagnetic signals. In addition, in some implementations, prior to transmitting the data, the controller can also determine whether data to be communicated is secure data, and only communicate the data (using the far-field communication interface) if it is not secure data. If the data is secure data, the controller will not communicate it using the far-field communication interface, but will wait until one of the body area network communication interface becomes available and is able to establish a communication link with acceptable quality of service.

For example, in one non-limiting implementation, communications within the body area network can use communication methods (such as magnetic induction) with limited energy boundary instead of communication methods (such as electromagnetic radiation) that can radiate far outside the body area network to minimize exposure. For instance, a device can communicate with other devices that are part of a BAN using BLE® technology when the device is located in a far-field coverage region and outside of a near-field coverage region, but can communicate with other devices that are part of the BAN using magnetic based wireless communication technology (e.g., Near Field Magnetic Inductive technology (NFMI) radio communication technology) when the device is located within a near-field coverage region. Using electromagnetic signals to communicate between devices, such as those use to communicate when using BLE® technologies, can provide a very good far-field solution for longer range communications. For example, electromagnetic signals work well for communications with wireless devices positioned more than 2 meters away from the body (e.g., for communications between an insulin pump and any wireless devices positioned more than 2 meters away from the body such as a dongle). While using electromagnetic signals to communicate can provide a very good far-field solution, they are not well-suited for shorter-range, near-field communications. However, magnetic signals, on the other hand, are not attenuated by things such as the human body or water. In general, magnetic signals can propagate through the human body and water as they do through the air. This makes magnetic signals a better solution to use when devices are communicating within a near-field coverage region. This can allow devices within the body area network to communicate, for example, through the human body and in water. For instance, magnetic-based wireless communications technologies, such as Near-Field Magnetic Inductive (NFMI) radio communication technology, can provide the necessary data rates for communications between an insulin pump and a CGM for closed-loop therapy. However, unlike BLE®, magnetic-based wireless communication does not suffer from human body blockage of RF signals, unpredictable fading of RF signals reflected off adjacent objects or other RF interferences that contribute to data packet loss through the wireless links. Magnetic-based communications can also propagate through water, making underwater wireless communications and therapy a reality. While the human body is made up primarily of "saltwater," which greatly attenuates electromagnetic wave propagation at BLE® frequencies, salt lowers dimagnetism of water and makes it transparent to magnetic-based communications. This can allow, for example, monitoring glucose level or maintaining closed-loop therapies while swimming, showering, sleeping in certain positions where there would normally be blockage by the human body, or being in open areas (e.g., parking lots, a soccer field, etc.).

Another issue with some body area networks is security. While security is desirable in any communication system, it is particularly important within a body area network. Within an insulin infusion system, the various devices can communicate various types of data that is encrypted, for example, to achieve a level of security. However, encrypted data is still capable of being intercepted by an eavesdropper, and then decrypted, at which point the security of that data is compromised and it is no longer secure. To explain further, even with strong encryption, a hacker can derive useful information by eavesdropping a sufficiently large number of wireless data broadcast over the air.

The disclosed embodiments can help improve security because devices are able to communicate only if they are within a traceable boundary near the body (also referred to herein as a near-field communication region). Any devices outside this boundary cannot communicate with devices that are within this traceable boundary (or near-field communication region) due to the rapid decay of the magnetic field outside the body area network. Instead of the field being proportional to the inverse square of the distance, as is the electric field from a point charge, the magnetic field is inversely proportional to the distance from the conductor or wire. To explain further, because magnetic signals decay quickly in comparison to electromagnetic signals, a clearly-defined, traceable boundary exists around the human body that is not hackable by anyone outside this secured communication "bubble." The same frequency can, therefore, be reused a short distance away, practically eliminating spectrum contention. For instance, with a variable link distance of around 1.5 meters, the data rate for NFMI radio communications can be 5 to 600 Kbps per frequency channel at around 13 MHz. Time division multiple access (TDMA) can provide for upward of 10 to 15 slots per channel. As such, the disclosed embodiments can help to provide improved wireless cybersecurity and reliability for patients.

In addition, as with any wireless network, it is desirable for the communication technology that is used to be power efficient so that batteries used to power the devices can last longer without needing to be replaced or recharged. The disclosed embodiments can help improve power efficiency and use less battery power because magnetic communications are many times more power efficient than electromagnetic communications (e.g., BLE® communications). For instance, in the non-limiting example described above, using NFMI radio communications for shorter-range, near-field communications (or near-body communications) between devices, and using BLE® for longer-range, far-field communications allows limited battery power on an insulin pump to be used more effectively.

Turning now to FIG. 1, one exemplary embodiment of an infusion system 100 includes, without limitation, a fluid infusion device (or infusion pump) 102, a sensing arrangement 104, a command control device (CCD) 106, and a computer 108. The components of an infusion system 100 may be realized using different platforms, designs, and configurations, and the embodiment shown in FIG. 1 is not exhaustive or limiting. In practice, the infusion device 102 and the sensing arrangement 104 are secured at desired locations on the body of a user (or patient), as illustrated in FIG. 1. In this regard, the locations at which the infusion device 102 and the sensing arrangement 104 are secured to the body of the user in FIG. 1 are provided only as a representative, non-limiting, example. The elements of the infusion system 100 may be similar to those described in U.S. Pat. No. 8,674,288, the subject matter of which is hereby incorporated by reference in its entirety.

In the illustrated embodiment of FIG. 1, the infusion device 102 is designed as a portable medical device suitable for infusing a fluid, a liquid, a gel, or other medicament into the body of a user. In exemplary embodiments, the infused fluid is insulin, although many other fluids may be administered through infusion such as, but not limited to, HIV drugs, drugs to treat pulmonary hypertension, iron chelation drugs, pain medications, anti-cancer treatments, medications, vitamins, hormones, or the like. In some embodiments, the fluid may include a nutritional supplement, a dye, a tracing medium, a saline medium, a hydration medium, or the like.

The sensing arrangement 104 generally represents the components of the infusion system 100 configured to sense, detect, measure or otherwise quantify a condition of the user, and may include a sensor, a monitor, or the like, for providing data indicative of the condition that is sensed, detected, measured or otherwise monitored by the sensing arrangement. In this regard, the sensing arrangement 104 may include electronics and enzymes reactive to a biological condition, such as a blood glucose level, or the like, of the user, and provide data indicative of the blood glucose level to the infusion device 102, the CCD 106 and/or the computer 108. For example, the infusion device 102, the CCD 106 and/or the computer 108 may include a display for presenting information or data to the user based on the sensor data received from the sensing arrangement 104, such as, for example, a current glucose level of the user, a graph or chart of the user's glucose level versus time, device status indicators, alert messages, or the like. In other embodiments, the infusion device 102, the CCD 106 and/or the computer 108 may include electronics and software that are configured to analyze sensor data and operate the infusion device 102 to deliver fluid to the body of the user based on the sensor data and/or preprogrammed delivery routines. Thus, in exemplary embodiments, one or more of the infusion device 102, the sensing arrangement 104, the CCD 106, and/or the computer 108 includes a transmitter, a receiver, and/or other transceiver electronics that allow for communication with other components of the infusion system 100, so that the sensing arrangement 104 may transmit sensor data or monitor data to one or more of the infusion device 102, the CCD 106 and/or the computer 108.

Still referring to FIG. 1, in various embodiments, the sensing arrangement 104 may be secured to the body of the user or embedded in the body of the user at a location that is remote from the location at which the infusion device 102 is secured to the body of the user. In various other embodiments, the sensing arrangement 104 may be incorporated within the infusion device 102. In other embodiments, the sensing arrangement 104 may be separate and apart from the infusion device 102, and may be, for example, part of the CCD 106. In such embodiments, the sensing arrangement 104 may be configured to receive a biological sample, analyte, or the like, to measure a condition of the user.

In some embodiments, the CCD 106 and/or the computer 108 may include electronics and other components configured to perform processing, delivery routine storage, and to control the infusion device 102 in a manner that is influenced by sensor data measured by and/or received from the sensing arrangement 104. By including control functions in the CCD 106 and/or the computer 108, the infusion device 102 may be made with more simplified electronics. However, in other embodiments, the infusion device 102 may include all control functions, and may operate without the CCD 106 and/or the computer 108. In various embodiments, the CCD 106 may be a portable electronic device. In addition, in various embodiments, the infusion device 102 and/or the sensing arrangement 104 may be configured to transmit data to the CCD 106 and/or the computer 108 for display or processing of the data by the CCD 106 and/or the computer 108.

In some embodiments, the CCD 106 and/or the computer 108 may provide information to the user that facilitates the user's subsequent use of the infusion device 102. For example, the CCD 106 may provide information to the user to allow the user to determine the rate or dose of medication to be administered into the user's body. In other embodiments, the CCD 106 may provide information to the infusion device 102 to autonomously control the rate or dose of medication administered into the body of the user. In some embodiments, the sensing arrangement 104 may be integrated into the CCD 106. Such embodiments may allow the user to monitor a condition by providing, for example, a sample of his or her blood to the sensing arrangement 104 to assess his or her condition. In some embodiments, the sensing arrangement 104 and the CCD 106 may be used for determining glucose levels in the blood and/or body fluids of the user without the use of, or necessity of, a wire or cable connection between the infusion device 102 and the sensing arrangement 104 and/or the CCD 106.

In some embodiments, the sensing arrangement 104 and/or the infusion device 102 are cooperatively configured to utilize a closed-loop system for delivering fluid to the user. Examples of sensing devices and/or infusion pumps utilizing closed-loop systems may be found at, but are not limited to, the following U.S. Pat. Nos. 6,088,608, 6,119,028, 6,589,229, 6,740,072, 6,827,702, 7,323,142, and 7,402,153 or United States Patent Application Publication No. 2014/0066889, all of which are incorporated herein by reference in their entirety. In such embodiments, the sensing arrangement 104 is configured to sense or measure a condition of the user, such as, blood glucose level or the like. The infusion device 102 is configured to deliver fluid in response to the condition sensed by the sensing arrangement 104. In turn, the sensing arrangement 104 continues to sense or otherwise quantify a current condition of the user, thereby allowing the infusion device 102 to deliver fluid continuously in response to the condition currently (or most recently) sensed by the sensing arrangement 104 indefinitely. In some embodiments, the sensing arrangement 104 and/or the infusion device 102 may be configured to utilize the closed-loop system only for a portion of the day, for example only when the user is asleep or awake.

Figure 2:
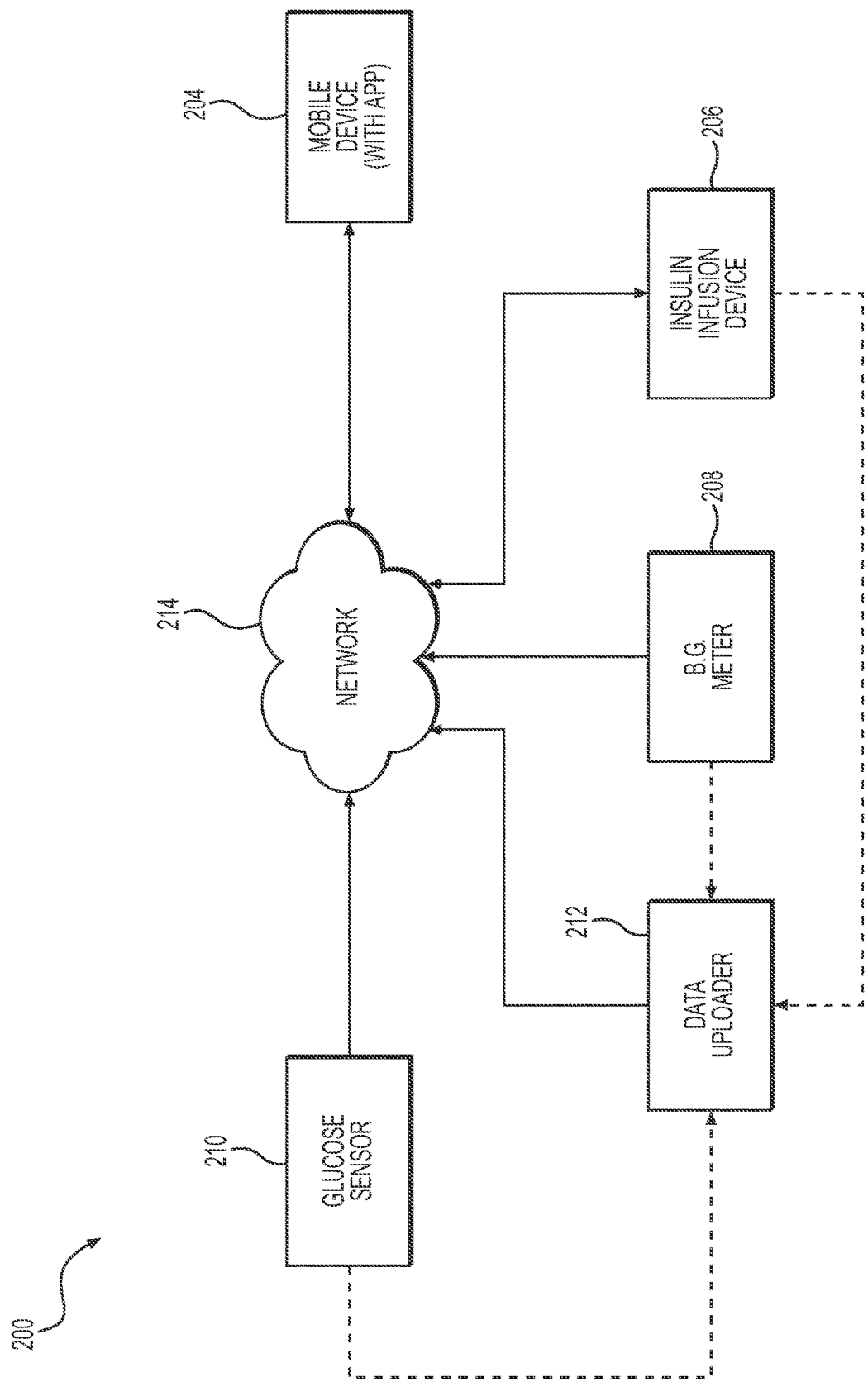
FIG. 2 is a simplified block diagram representation of an exemplary embodiment of a communication system.

FIG. 2 is a simplified block diagram representation of an exemplary embodiment of a communication system 200 that is suitably configured to support the techniques and methodologies described in more detail below. The system 200 supports users of insulin infusion devices, and performs various techniques and methods to help users (patients, caregivers, healthcare providers, parents, etc.) manage the use of insulin infusion devices. It should be appreciated that FIG. 2 depicts one possible implementation of a communication system, and that other arrangements, architectures, and deployments can be provided if so desired. The system 200 (which has been simplified for purposes of illustration) generally includes or cooperates with the following components, without limitation: a mobile device 204; an insulin infusion device 206; a blood glucose meter 208; a continuous glucose sensor 210; and an optional data uploader 212. The mobile device 204 is a client device that is owned or operated by the user, i.e., a diabetic patient. The insulin infusion device 206, the blood glucose meter 208, and the glucose sensor 210 are components of an insulin infusion system that is used by the patient to treat diabetes. The system 200 may also include or cooperate with the optional data uploader component 212.

The various components of the system 200 can be used to collect and analyze input data for the patient that can originate from various sources, including an insulin infusion device, a glucose sensor or meter, a mobile device operated by a user of the insulin infusion device, or other components or computing devices that are compatible with the system, such as a data uploader. These and other alternative arrangements are contemplated by this disclosure. To this end, some embodiments of the system may include additional devices and components that serve as data sources, data processing units, etc. For example, the system may include any or all of the following elements, without limitation: computer devices or systems; patient monitors; healthcare provider systems; data communication devices; and the like. It should be appreciated that the insulin infusion device 206 can be an optional component in some applications (for example, for Type 2 diabetes patients). For such applications, another diabetes management device and/or the mobile device 204 can function in an equivalent manner to support the system 200.

At a minimum, the mobile device 204 is communicatively coupled to a network 214. In certain embodiments, the insulin infusion device 206, the blood glucose meter 208, and/or the continuous glucose sensor 210 are also communicatively coupled to the network 214 to facilitate the uploading of relevant data to a remote server system (not illustrated). Alternatively, or additionally, the insulin infusion device 206, the blood glucose meter 208, and the continuous glucose sensor 210 provide relevant data to the data uploader component 212, which in turn uploads the data to other systems (not illustrated) via the network 214.

FIG. 2 depicts the network 214 in a simplified manner. In practice, the system 200 may cooperate with and leverage any number of wireless and any number of wired data communication networks maintained or operated by various entities and providers. Accordingly, communication between the various components of the system 200 may involve multiple network links and different data communication protocols. In this regard, the network 214 can include or cooperate with any of the following, without limitation: a local area network; a wide area network; the Internet; a personal area network; a cellular communication network; a satellite communication network; a video services or television broadcasting network; a network onboard a vehicle; or the like. In addition, the various components can also communicate directly with each other using NFMI radio communications; NFeMI radio communications, BLE® communications, classical Bluetooth® (BT) communications, WLAN (or "Wi-Fi") communications, or indirectly with each other using WLAN or cellular communications, as will be described below. The components of the system may be suitably configured to support a variety of wireless and wired data communication protocols, technologies, and techniques as needed for compatibility with the network 214.

The mobile device 204 can be realized using a variety of different device platforms. For example, the mobile device 204 can be implemented as any of the following, without limitation: a cellular telephone or smartphone; a portable computer (e.g., a laptop, a tablet, or a netbook computer); a portable media player; a portable video game device; a portable medical device; a navigation device such as a global positioning system (GPS) device; a wearable computing device; an electronic toy or game; etc. In accordance with certain exemplary embodiments, the mobile device 204 supported by the system 200 is implemented as a computer-based or processor-based component. For simplicity and ease of illustration, FIG. 2 depicts only one mobile device 204. In practice, however, the system 200 is suitably configured to support a plurality of mobile devices 204, where the patient or user owns or operates at least one of the supported mobile devices 204. An exemplary embodiment of a device suitable for implementing the mobile device 204 is described below with reference to FIGS. 3 and 4.

The remainder of this description assumes that the mobile device 204 is a smartphone used by the particular patient. To this end, the configuration and general functionality of the mobile device 204 can be substantially consistent with conventional smartphone design. In this regard, a suitably designed mobile app is installed on the mobile device 204 to allow the patient to receive, view, and interact with messages and notifications provided by the system. The mobile app installed on the mobile device 204 can also be utilized to provide relevant data to other systems (not illustrated) for storage and analysis. For example, the mobile app can manage and upload the following information, without limitation: calendar data (time of day, day of the week, month, season, etc.); user profile data; GPS data that indicates the geographic position of the mobile device 204; map or navigation data associated with operation of the mobile device 204; user-entered meal consumption, food content, and/or food ingredient data; user-entered carbohydrate data; user-entered exercise related data; user-entered medication related data; user response data associated with the receipt of glycemic insight messages; user feedback related to glycemic insight messages; accelerometer data; contacts list information; web browser data; consumer purchasing data; and the like.

In certain embodiments, the insulin infusion device 206 is a portable patient-worn or patient-carried component that is operated to deliver insulin into the body of the patient via, for example, an infusion set. In accordance with certain exemplary embodiments, each insulin infusion device 206 supported by the system 200 is implemented as a computer-based or processor-based component. For simplicity and ease of illustration, FIG. 2 depicts only one insulin infusion device 206. In practice, however, the system 200 is suitably configured to support a plurality of insulin infusion device 206, wherein each patient or user owns or operates at least one of the insulin infusion devices 206. An exemplary embodiment of a device suitable for implementing the insulin infusion device 206 is described below with reference to FIGS. 3 and 4.

The system 200 obtains input data from one or more sources, which may include various diabetes management devices (an insulin infusion device, a continuous glucose monitoring device, a glucose sensor, a monitor device, or the like). In this regard, the insulin infusion device 206 represents a source of input data for the system 200. In certain embodiments, the insulin infusion device 206 provides data that is associated with its operation, status, insulin delivery events, and the like. As mentioned previously, relevant data generated or collected by the insulin infusion device 206 can be transmitted directly or indirectly to other components of the system including the data uploader component 212, depending on the particular implementation of the system 200. The particular type of data provided by the insulin infusion device 206 is described in more detail below.

The patient or user can own or operate the blood glucose meter 208. The blood glucose meter 208 is configured to measure the blood glucose level of a user by analyzing a blood sample. For example, the blood glucose meter 208 may include a receptacle for receiving a blood sample test strip. In this regard, the user inserts a test strip into the blood glucose meter 208, which analyzes the sample and displays a blood glucose level corresponding to the test strip sample. The blood glucose meter 208 may be configured to communicate the measured blood glucose level to the insulin infusion device 206 for storage and processing, to the mobile device 204, or to the data uploader component 212. In some scenarios, the patient is responsible for entering each blood glucose measurement into the insulin infusion device 206. Ultimately, the measured blood glucose data can be provided to any components of the system for analysis.

The glucose sensor 210 can be owned or operated by the patient or user. The glucose sensor 210 is suitably configured to measure a glucose level (interstitial) of the patient in real time. The glucose sensor 210 may include a wireless transmitter that facilitates transmission of the sensor glucose data to other devices, such as the insulin infusion device 206 or the data uploader component 212 or other components of the system, where the sensor glucose data can be received for further processing.

Depending on the particular embodiment and application, the system 200 can include or cooperate with other devices, systems, and sources of input data. Devices within the system 200 may be configured to support the transmission of data to various external devices, such as, without limitation: a stationary monitor device, such as a bedside monitor or a piece of hospital monitoring equipment; a portable computer, such as a laptop PC, a palmtop PC, or a tablet PC; a stationary computer, such as a desktop PC; a personal digital assistant, which may also be a portable email device; one or more additional computing devices or databases; or the like. The above list of possible external devices is not exhaustive, and an implementation of the system 200 can be designed to accommodate communication with other systems, equipment, computing devices, components, and elements that are external to the system 200. For example, in certain embodiments the system 200 includes one or more sources of contextual information or data, which may include, without limitation: activity tracker devices; meal logging devices or apps; mood tracking devices or apps; and the like.

The system 200 includes a local infusion system having one or more local devices configured to wirelessly communicate with each other. This description may refer to the local infusion system as a "personal area network" or a "body area network" of its constituent devices. These local devices may be configured to transmit and receive local communications within the local infusion system, where such local communications are transmitted and received in accordance with one or more specified local data communication protocols. For example, local communications may be exchanged between local devices using one or more wireless data communication protocols (which may leverage RF, infrared, magnetic induction, or other wireless techniques) and/or using one or more wired data communication protocols. Thus, one or more of the local devices can be considered to be a wireless medical device in the context of this description. The local infusion system may be flexibly configured such that any given local device can communicate with any other local device, and a communication link or path between two local devices may be unidirectional or bidirectional. FIG. 2 depicts an exemplary embodiment where each communication link or path is bidirectional (represented by double headed arrows).

Moreover, the local devices in the local infusion system may be capable of communication (unidirectional or bidirectional) with one or more "external" devices that are not considered to be part of the local infusion system. The manner in which a given local device within the local infusion system communicates with a given external device may vary depending upon the particular configuration of the system 200, the characteristics of the local device, and the characteristics of the external device. For example, data may be routed between the local infusion system and an external device using one data communication network, using a plurality of data communication networks, using a direct wireless or wired connection, or the like.

Figure 3:
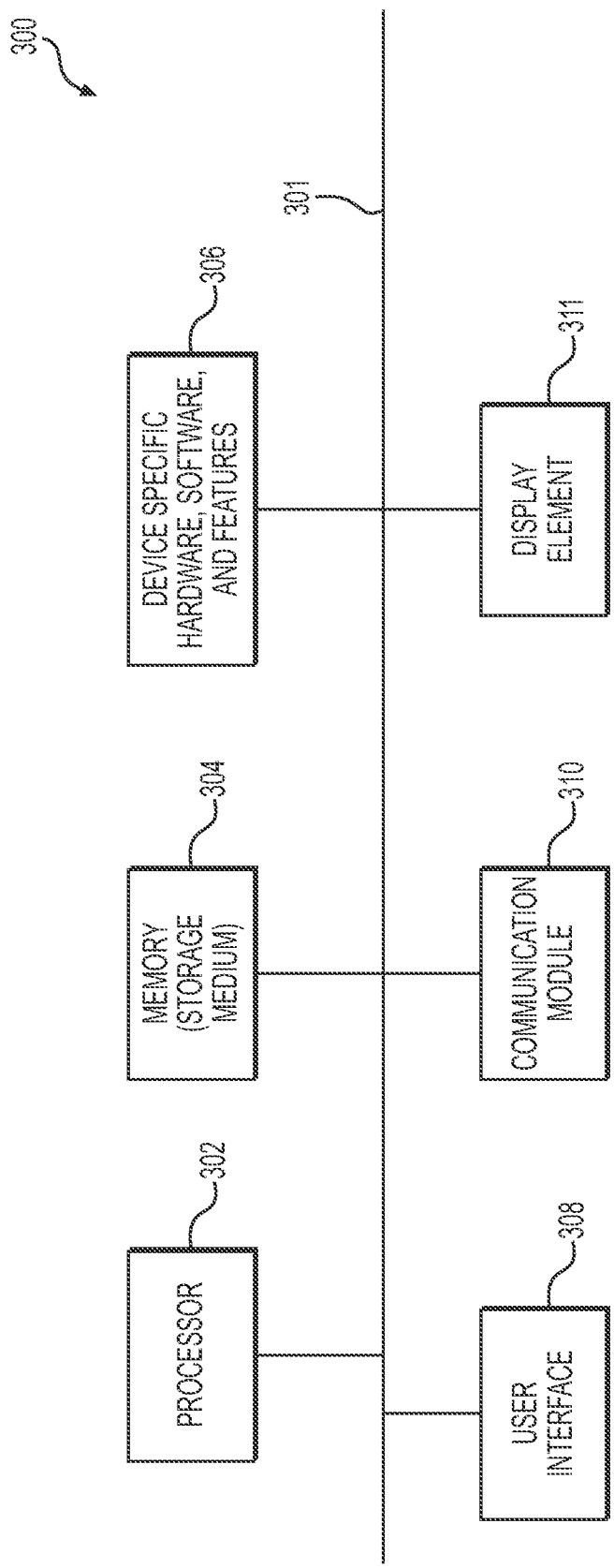
FIGS. 3 and 4 are collectively a simplified block diagram representation of an exemplary embodiment of a computer-based or processor-based device in accordance with the disclosed embodiments.
Figure 4:
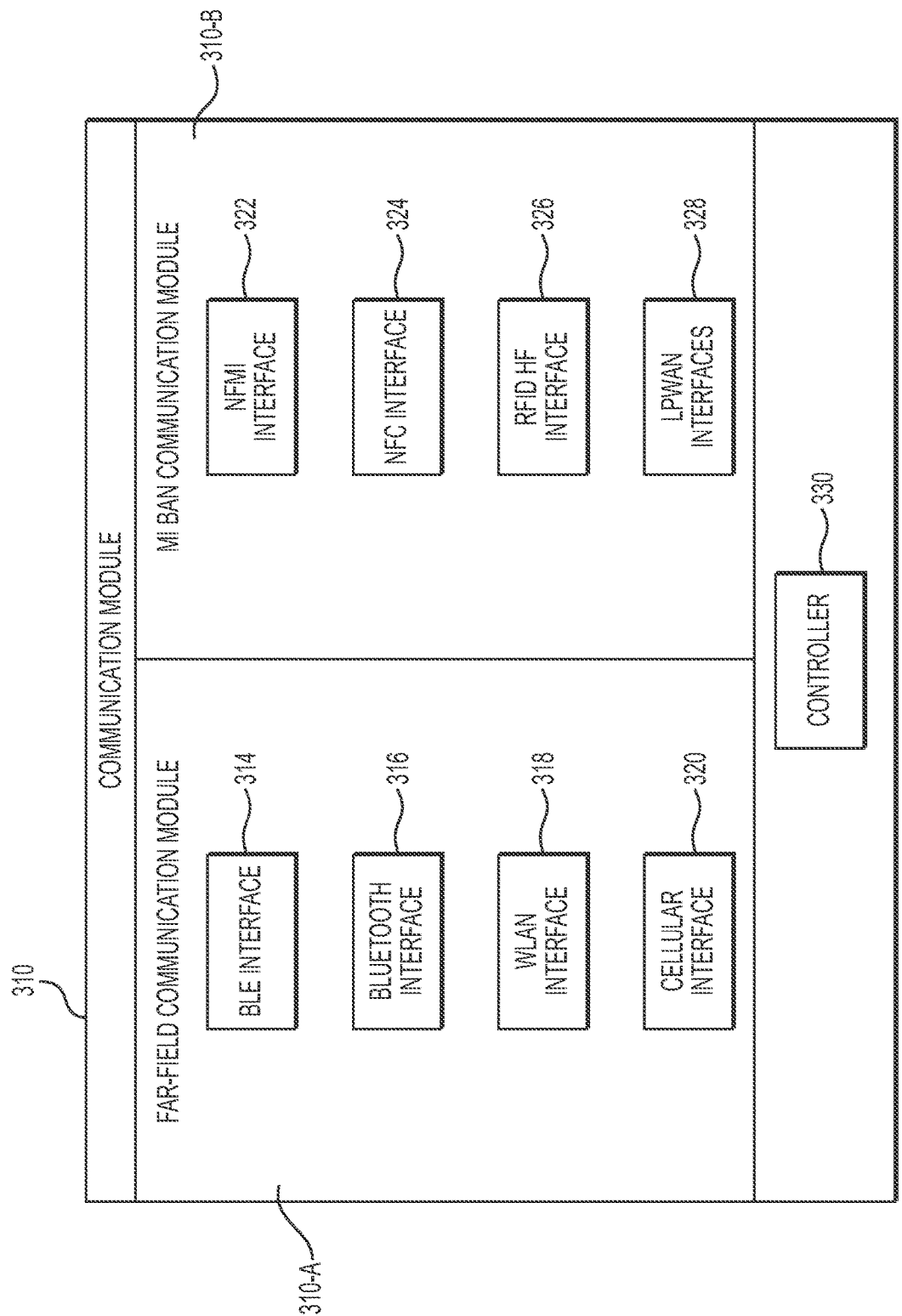

As mentioned above, the system 200 includes or cooperates with computer-based and/or processor-based components having suitably configured hardware and software written to perform the functions and methods needed to support the features described herein. For example, the mobile device 204, the insulin infusion device 206, the blood glucose meter 208 and the data uploader component 212 can be realized as an electronic processor-based component. An exemplary embodiment of a device suitable for implementing the various components of the system will described below with reference to FIGS. 3 and 4. In this regard, FIGS. 3 and 4 are collectively simplified block diagram representations of an exemplary embodiment of a computer-based or processor-based device 300 that is suitable for deployment in the system shown in FIG. 2.

The illustrated embodiment of the device 300 is intended to be a high-level and generic representation of one suitable platform. In this regard, any of the computer-based or processor-based components of the system 200 can utilize the architecture of the device 300. The illustrated embodiment of the device 300 generally includes, without limitation: at least one processor 302; a suitable amount of memory 304; device-specific hardware, software, firmware, and/or features 306; a user interface 308; a communication module 310; and a display element 311. Of course, an implementation of the device 300 may include additional elements, components, modules, and functionality configured to support various features that are unrelated to the subject matter described here. For example, the device 300 may include certain features and elements to support conventional functions that might be related to the particular implementation and deployment of the device 300. In practice, the elements of the device 300 may be coupled together via a bus or any suitable interconnection architecture 301.

The processor 302 may be implemented or performed with a general-purpose processor, a content addressable memory, a digital signal processor, an application specific integrated circuit, a field programmable gate array, any suitable programmable logic device, discrete gate or transistor logic, discrete hardware components, or any combination designed to perform the functions described here. Moreover, the processor 302 may be implemented as a combination of computing devices, e.g., a combination of a digital signal processor and a microprocessor, a plurality of microprocessors, one or more microprocessors in conjunction with a digital signal processor core, or any other such configuration.

The memory 304 may be realized as RAM memory, flash memory, EPROM memory, EEPROM memory, registers, a hard disk, a removable disk, a CD-ROM, or any other form of storage medium known in the art. In this regard, the memory 304 can be coupled to the processor 302 such that the processor 302 can read information from, and write information to, the memory 304. In the alternative, the memory 304 may be integral to the processor 302. As an example, the processor 302 and the memory 304 may reside in an ASIC. At least a portion of the memory 304 can be realized as a computer storage medium, e.g., a tangible computer-readable medium having computer-executable instructions stored thereon. The computer-executable instructions, when read and executed by the processor 302, cause the device 300 to perform certain tasks, operations, functions, and processes that are specific to the particular embodiment. In this regard, the memory 304 may represent one suitable implementation of such computer-readable media. Alternatively, or additionally, the device 300 could receive and cooperate with computer-readable media (not separately shown) that is realized as a portable or mobile component or platform, e.g., a portable hard drive, a USB flash drive, an optical disc, or the like.

The device-specific hardware, software, firmware, and features 306 may vary from one embodiment of the device 300 to another. For example, the device-specific hardware, software, firmware, and features 306 will support: smartphone functions and features when the device 300 is realized as a mobile telephone; conventional personal computer functions and features if the device 300 is realized as a laptop or tablet computer; insulin pump operations when the device 300 is realized as an insulin infusion device; etc. In practice, certain portions or aspects of the device-specific hardware, software, firmware, and features 306 may be implemented in one or more of the other blocks depicted in FIGS. 3 and 4.

The user interface 308 may include or cooperate with various features to allow a user to interact with the device 300. Accordingly, the user interface 308 may include various human-to-machine interfaces, e.g., a keypad, keys, a keyboard, buttons, switches, knobs, a touchpad, a joystick, a pointing device, a virtual writing tablet, a touch screen, a microphone, or any device, component, or function that enables the user to select options, input information, or otherwise control the operation of the device 300. The user interface 308 may include one or more graphical user interface (GUI) control elements that enable a user to manipulate or otherwise interact with an application via the display element 311.

The communication module 310 facilitates data communication between the device 300 and other components as needed during the operation of the device 300. In the context of this description, the communication module 310 can be employed to transmit or stream device-related control data, patient-related data, device-related status or operational data, glycemic insight messages and notifications, and the like. It should be appreciated that the particular configuration and functionality of the communication module 310 can vary depending on the hardware platform and specific implementation of the device 300. Accordingly, the communication module 310 is utilized to obtain input data from various sources, and to send output data to other components or devices that are described above with reference to FIGS. 1 and 2. In practice, an embodiment of the device 300 may support wireless data communication and/or wired data communication, using various data communication protocols. For example, the communication module 310 could support one or more wireless data communication protocols, techniques, or methodologies, including, without limitation: RF; IrDA (infrared); Bluetooth®; ZigBee® (and other variants of the IEEE 802.15 protocol); IEEE 802.11 (any variation); IEEE 802.16 (WiMAX or any other variation); Direct Sequence Spread Spectrum; Frequency Hopping Spread Spectrum; cellular/wireless/cordless telecommunication protocols; wireless home network communication protocols; paging network protocols; magnetic induction; satellite data communication protocols; wireless hospital or health care facility network protocols such as those operating in the WMTS bands; GPRS; and proprietary wireless data communication protocols such as variants of Wireless USB. Moreover, the communication module 310 could support one or more wired/cabled data communication protocols, including, without limitation: Ethernet; powerline; home network communication protocols; USB; IEEE 2394 (Firewire); hospital network communication protocols; and proprietary data communication protocols. In one particular implementation that is illustrated in FIG. 4, the communication module 310 includes a far-field communication module 310-A and a body area network communication module 310-B, and a controller 330.

The far-field communication module 310-A includes various far-field communication interfaces that can be used to communicate electromagnetic signals to other devices that are part of a body area network. In this non-limiting example, various far-field communication interfaces can include, but are not limited to, a Bluetooth low energy (BLE®) communication interface 314, a classical Bluetooth® (BT) communication interface 316, a wireless local area network (WLAN) communication interface 318 (e.g., a WiFi interface), and a cellular communication interface 320. The above-mentioned communication interfaces can comply with any known standards. For example, the BLE® communication interface 314 can communicate in compliance with any Bluetooth® release (e.g., versions 1.0 through 5.1), and any physical (PHY) layer specifications defined therein. For instance, Bluetooth® 5.0 includes three PHY layer variations called LE 1M, LE 2M and LE Coded. Each PHY variant has its own particular characteristics and was designed with specific aims in mind. As another non-limiting example, the BLE® communication interface 314 communicate in compliance with a Bluetooth® mesh networking protocol (defined in Mesh Profile Specification and Mesh Model Specification which was adopted on Jul. 13, 2017). The Bluetooth® mesh networking protocol is a protocol based upon Bluetooth Low Energy® that allows for many-to-many communication over Bluetooth® radio.

When a signal from a far-field communication interface is transmitted by an antenna, it is attenuated over distance to the point that the signal cannot be effectively detected. This is called far-field transmission, and works well if the signal needs to be transmitted over a long distance. However, far-field communication interfaces can have problems if the wireless communication needs to be very low power and confines to a fairly short distance near body areas. Improper placement of devices close to a human body may result in a detuned antenna input impedance, reduced antenna efficiency, and distorted antenna radiation pattern. Penetration of electromagnetic signals generated by far-field communication interfaces into the human body is another problem because electromagnetic signals can be quickly absorbed and greatly attenuated due to the very conductive body tissues. In addition, interference can be very high due to coexistence of multiple far-field communication interfaces (e.g., BT, BLE®, Wi-Fi, and ZigBee®) that operate in the same frequency band. Power consumption can also limit continuous operation. Lastly, far-field communication interface can present potential security problems because electromagnetic signals can be intercepted and decrypted after propagating into free space.

On the other hand, the body area network communication module 310-B includes various near-field communication interfaces that can be used to communicate magnetic signals to other devices that are part of a body area network. In this non-limiting example, various near-field communication interfaces can include, but are not limited to, a near field magnetic inductive (NFMI) radio communication interface 322, a near-field electromagnetic induction (NFeMI) radio communication interface (not illustrated), a near field communication (NFC) interface 324, an RFID high-frequency (HF) communication interface 326, and one or more low power wide area network (LPWAN) communication interfaces 328. A near-field communication interface 322 can provide a more reliable, a more secure, and a much lower power radio link within, on, and in the immediate proximity of a human body.

For example, NFMI is a short-range wireless technology that communicates using a tightly coupled magnetic field among devices. NFMI enables human body friendly, reliable, secure, and power efficient wireless communication. As used herein, the term "Near-Field Magnetic Induction (NFMI) radio communication system" can refer to a short range wireless physical layer that communicates by coupling a tight, low-power, non-propagating magnetic field between devices. A transmitter coil in one device can modulate a magnetic field which is measured by a receiver coil in another device. To explain further, in NFMI-based communication systems, a modulated signal that is sent out from a transmitter coil is in the form of a magnetic field. This magnetic field induces voltage on the receiving coil, which in turn will be measured by an NFMI receiver. NFMI radio communication systems differ from other wireless communications in that most conventional wireless RF systems use an antenna to generate, transmit, and propagate an electromagnetic wave, where all of the transmission energy is designed to radiate into free space. This type of transmission is referred to as "far-field." NFMI systems are designed to contain transmission energy within the localized magnetic field. This magnetic field energy resonates around the communication system, but does not radiate into free space. To explain further, the power density of NFMI signals attenuate at a rate inversely proportional to the distance to the sixth power compared to the second power for Bluetooth® signals. This means for the same distance, the power density of NFMI signals is 10000 times weaker than Bluetooth® signals provided that both transmitting power are equal. This type of wireless transmission is referred to as "near-field." Various modulation schemes used in typical RF communications (e.g., amplitude modulation, phase modulation, and frequency modulation) can also be used in near-field magnetic induction communication system.

As used herein, the term "near-field electromagnetic induction (NFeMI) radio communication interface" can refer to a communication interface that can operate near a human body by means of a combination of a magnetic field and electric field without the use of transversal radiating waves. Such NFEMI systems improve a wearable device's signal link budget and extend their range to a complete human body. Whereas RF wireless communication may be accomplished by propagating an RF plane wave through free space, NFEMI communication utilizes non-propagating quasi-static fields.

As used herein, the term "Near-field communication (NFC)" can refer to a set of communication protocols and data exchange formats that enable two or more electronic devices (e.g., a medical device such as an insulin pump and a portable device such as a smartphone) to establish communication with each other by bringing them within a short separation range of each other (e.g., 2 meters or less). NFC allows one- and two-way communication between endpoints, suitable for many applications. NFC uses electromagnetic induction between two loop antennas (located within each other's near-field) to effectively form an air-core transformer that allows them to exchange information. The NFC interface 324 operates based on similar principles as the NFMI interface 322 and uses the same high-frequency (HF) band. However, NFMI extends the range of NFC (e.g., from a distance of 1-4 inches for NFC, to up to 9 feet for NFMI). At around 13 MHz, NFMI provides a data rate of over 400 Kbps per frequency channel, up to 10 separate frequency channels and 10 sub-channels per frequency channel using time division (e.g., a hundred separate wireless links inside a single WBAN). In one non-limiting implementation, NFC-enabled devices that are described herein can exchange information in accordance with any NFC standards that cover communications protocols and data exchange formats. NFC standards cover communications protocols and data exchange formats and are based on existing radio-frequency identification (RFID) standards including ISO/IEC 14443. The standards include ISO/IEC 18092 and those defined by the NFC Forum. In addition to the NFC Forum, the GSM Association (GSMA) group defined a platform for the deployment of GSMA NFC Standards within mobile handsets.

RFID systems can operate in low frequency (LF), high frequency (HF), and ultra-high frequency (UHF) bands, and thus can be categorized by the frequency band within which they operate: low frequency, high frequency, and ultra-high frequency. In addition, there are also two broad categories of systems—passive and active RFID. The LF band covers frequencies from 30 KHz to 300 KHz (e.g., some LF RFID systems operate at 125 KHz, while others operate at 134 KHz). The RFID HF communication interface 326 can operate in a HF band that ranges from 3 to 30 MHz, with communications ranges between 10 cm and 1 m. There are several HF RFID standards, such as the ISO 15693 standard for tracking items, and the ECMA-340 and ISO/IEC 18092 standards for Near Field Communication (NFC), the ISO/IEC 14443 A and ISO/IEC 14443 standards. The UHF frequency band covers the range from 300 MHz to 3 GHz, and the range of some UHF systems can be as long as 12 m with faster data transfer rates than LF or HF. The UHF frequency band is regulated by a single global standard called the ECPglobal Gen2 (ISO 18000-63) UHF standard.

The low power wide area network (LPWAN) communication interfaces 328 can include interfaces such as a Long Term Evolution for Machines (LTE-M) communication interface (LTE-Cat M1) and/or a narrowband-IoT (NB-IoT) communication interface (not illustrated). NB-IOT and LTE-M are two newer low power wide area (LPWA) technologies that were developed for IOT applications. Both are protocols for low bandwidth cellular communications that connect to the internet devices that need to transmit small amounts of data, with the lower costs (both hardware and subscription) and the higher battery life.

The various communication interfaces that are shown in FIG. 4 are non-limiting, and can be implemented in accordance with any known standards including those mentioned above. However, it should be appreciated that the number of communication interfaces that are included as part of the communication module 310 can vary depending on the implementation. Furthermore, the embodiment shown in FIG. 4 is non-limiting and many other types of communication interfaces can be included depending on the implementation.

As will be described below, the controller 330 is configured to control which ones of the communication interfaces are selected and used by a device or component of the wireless body area network to communicate data with other devices or components that are part of the wireless body area network. For example, the controller 330 is configured to select which one of the communication interfaces is to be used at any particular time and switch between which one of the communication interfaces is enabled and used by a device or component of the wireless body area network to communicate data with other devices or components that are part of the wireless body area network.

As will be described in greater detail below, depending on a device's proximity to the body area network, the controller 330 can select any of the various communication interfaces 314, 316, 318, 320, 322, 324, 326, 328 shown in FIG. 4 to use for communications with other devices that are part of the body area network. The controller 330 can seamlessly switch between the various communication interfaces 314, 316, 318, 320, 322, 324, 326, 328 based on factors such as quality of service of the communication link with another device, the security type of the data that is being communicated to the other device, etc. In this regard quality of service can be measured using any standard quality of service performance metrics (e.g., RSSI, packet loss, packet error rate (PER), bit rate, bit error rate, latency, throughput, transmission delay, availability, jitter, etc.) and compared to a threshold. Quality of service metrics can also include metrics such as as service response time, loss, signal-to-noise ratio, crosstalk, echo, interrupts, frequency response, and so on. Quality of service (QoS) is the description or measurement of the overall performance of a service, particularly the performance seen by the users of the network.

When the quality of service is greater than or equal to the threshold, the device can utilize a particular communication interface. When the quality of services is less than the threshold, the controller 330 can then determine an appropriate communication interface to switch to that will achieve the desired quality of service that is greater than or equal to the threshold. In addition, in some embodiments, once the controller 330 determines that the quality of service over one of the communication interfaces is greater than or equal to the threshold, the controller can also determine the type of data that is being communicated by the device, and if it is a high security datatype, the controller 330 can also restrict communication to one of the body area network communication interfaces 322, 324, 326, 328 such that communications can only take place within traceable security boundary, as defined by the body area network, where the wireless energy has not degraded to a negligible level. In other words, when the type of data being communicated is a high security datatype, the controller 330 will only utilize one of the body area network communication interfaces 322, 324, 326, 328 to help ensure security of the data that's being communicated.

Referring again to FIG. 3, the display element 311 is suitably configured to enable the device 300 to render and display various screens, insight messages, notifications, GUIs, GUI control elements, drop down menus, auto-fill fields, text entry fields, message fields, or the like. Of course, the display element 311 may also be utilized for the display of other information during the operation of the device 300, as is well understood. Notably, the specific configuration, operating characteristics, size, resolution, and functionality of the display element 310 can vary depending upon the practical implementation of the device 300. For example, if the device 300 is a laptop computer, then the display element 311 may be a relatively large monitor. Alternatively, if the device 300 is a cellular telephone device (e.g., smartphone), then the display element 311 may be a relatively small integrated display screen, such as a touch-sensitive screen.

Figure 5:
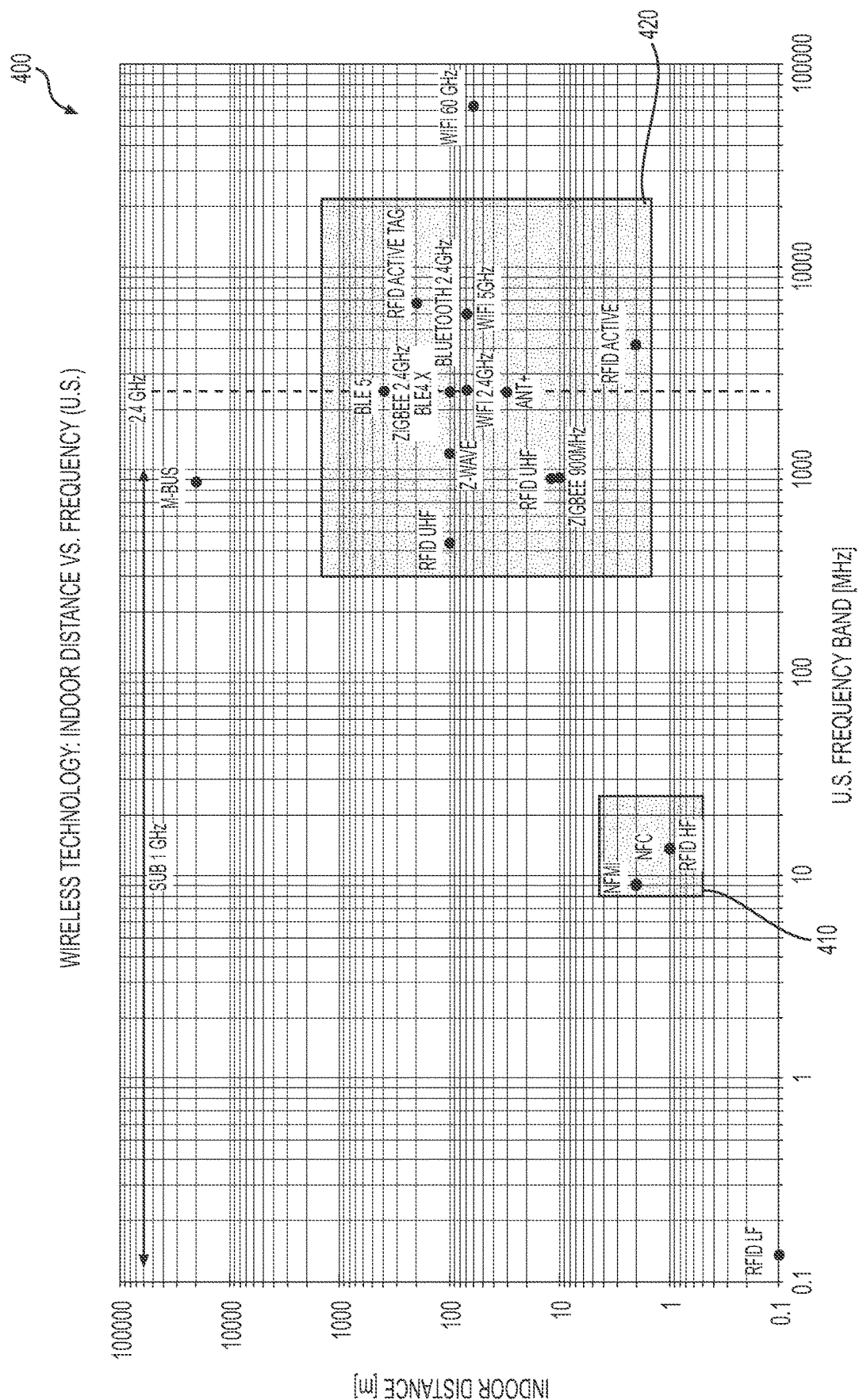
FIG. 5 is a graph that shows frequency bands and communication ranges for various communication interfaces that can be utilized in conjunction with the disclosed embodiments.

FIG. 5 is a graph that shows frequency bands and communication ranges for various communication interfaces that can be utilized in conjunction with the disclosed embodiments. These can be grouped into two groups as was described above (e.g., far-field communication interfaces 310-A, and body area network communication interfaces 310-B) with reference to FIG. 4. In FIG. 5, communication interfaces within rectangle 410 are examples of body area network communication interfaces 310-B (e.g., NFMI, NFeMI, NFC, RFID HF), communication interfaces within rectangle 420 are examples of far-field communication interfaces 310-A (e.g., RFID UHF, Z wave, ZigBee® 2.4 GHz, BLE® 5, BLE® 4.x, RFID Active Tag, Bluetooth® 2.4 GHz, WiFi 2.4 GHz, WiFi 5 GHz, WiFi 60 GHz, ANT+, RFID Active, ZigBee® 900 MHz).

FIG. 6 is a table that shows characteristics of various communication standards in accordance with one non-limiting implementation. FIG. 6 is provided to show non-limiting possible examples of the characteristics of these various communication standards including operating frequency (in megahertz (MHz)), data rate (in kilo bytes per second (kbps)), and range (in meters (m)). For example, column 2 illustrates characteristics of a communication interface that complies with an NFMI radio communication standard, column 3 illustrates characteristics of a communication interface that complies with a near field communication (NFC) standard, column 4 illustrates characteristics of a communication interface that complies with a classical Bluetooth® (BT) standard, and column 4 illustrates characteristics of a communication interface that complies with a BLE® communication standard.

Figure 7:
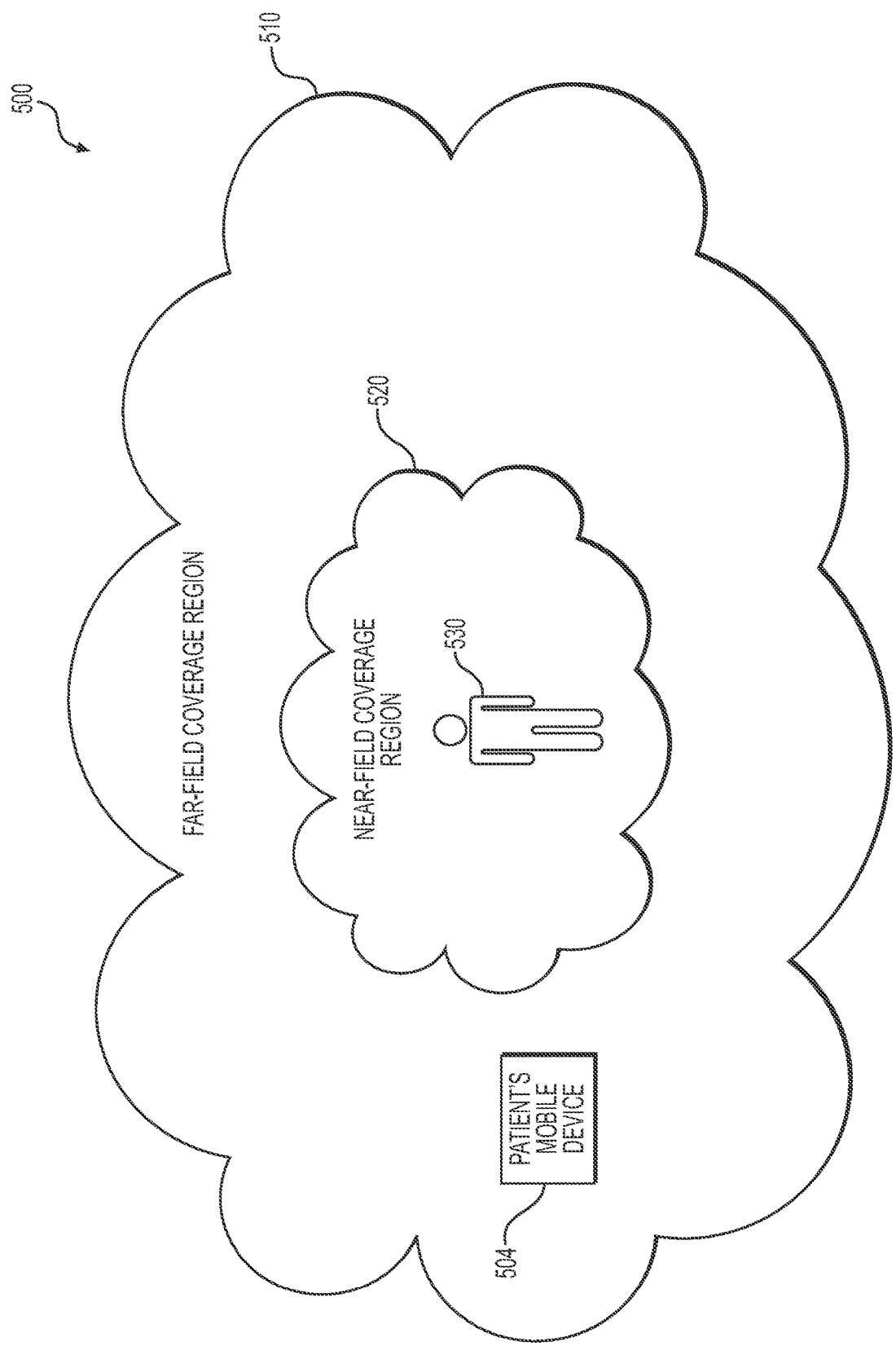
FIGS. 7 and 8 illustrate a communication environment in accordance of the disclosed embodiments.
Figure 8:
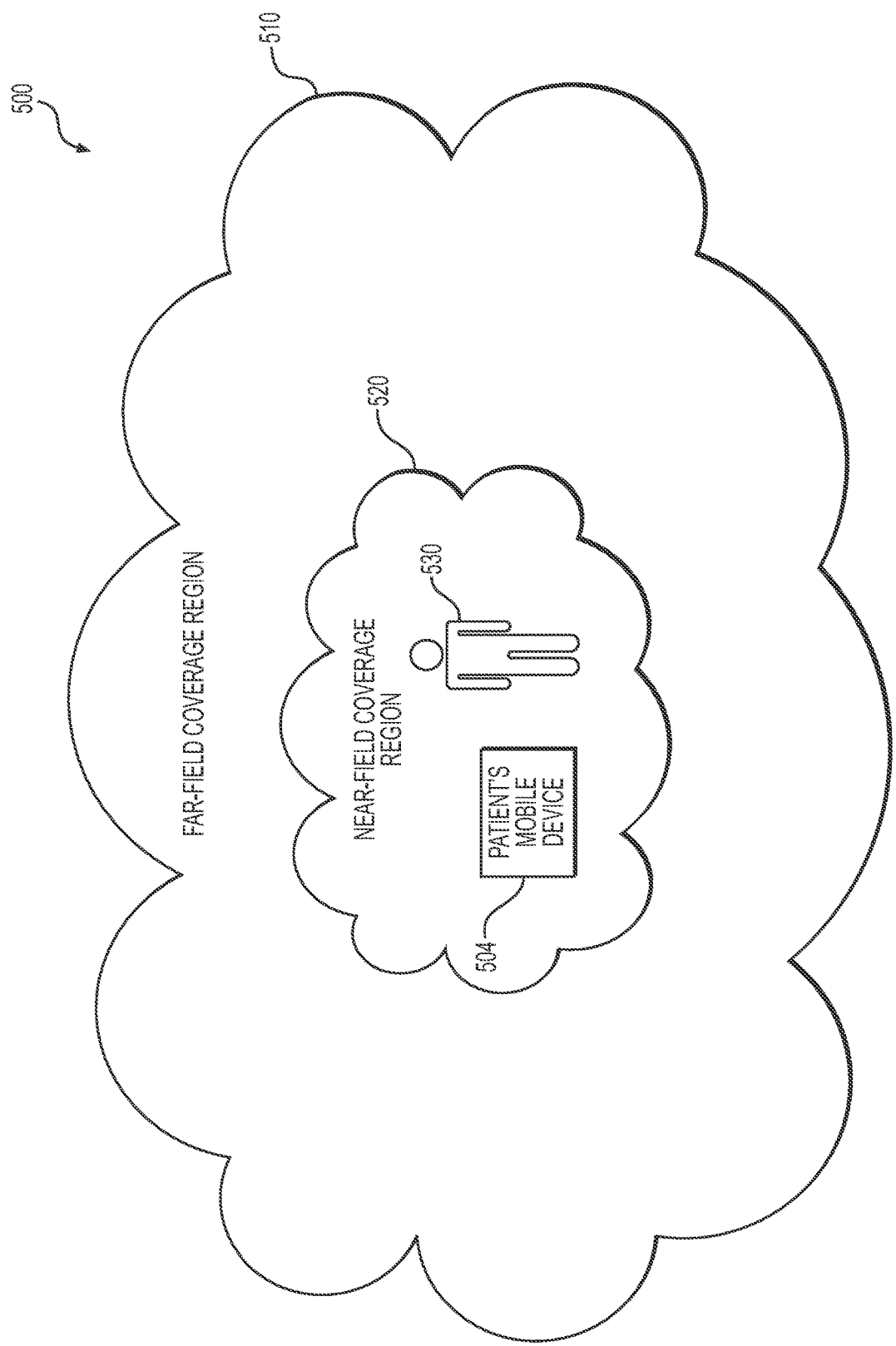

FIGS. 7 and 8 illustrate a communication environment 500 in accordance of the disclosed embodiments. The communication environment 500 can include a far-field coverage region 510 and a near-field coverage region 520, which can also be referred to as a BAN coverage region herein. Although not illustrated in FIGS. 7 and 8, the communication environment 500 can also include coverage regions associated with any of the communications technologies that are described herein.

The near-field and far-field are regions of the electromagnetic field (EM) around an object, such as a transmitting antenna. The far-field is the region in which the field acts as "normal" electromagnetic radiation. The far-field region is dominated by electric or magnetic fields with electric dipole characteristics. In the far-field region of an antenna, radiated power decreases as the square of distance, and absorption of the radiation does not feed back to the transmitter. Also known as the radiation-zone field, the far-field carries a relatively uniform wave pattern. The radiation zone is important because far-fields in general fall off in amplitude by 1/r, where r is the distance measured away from the transmitter. This means that the total energy per unit area at a distance r is proportional to $1/r^2$. The area of the sphere is proportional to $r^2$, so the total energy passing through the sphere is constant. This means that the far-field energy actually escapes to infinite distance (it radiates).

The near-field is governed by multipole type fields, which can be considered as collections of dipoles with a fixed phase relationship. The boundary between the two regions is only vaguely defined, and it depends on the dominant wavelength ($\lambda$) emitted by the source and the size of the radiating element. In the near-field region, absorption of radiation does affect the load on the transmitter. In the far-field region, each part of the EM field (electric and magnetic) is "produced by" (or associated with) a change in the other part, and the ratio of electric and magnetic field intensities is simply the wave impedance. However, in the near-field region, the electric and magnetic fields can exist independently of each other, and one type of field can dominate the other. Non-radiative 'near-field' behaviors of electromagnetic fields dominate close to the antenna or scattering object, while electromagnetic radiation 'far-field' behaviors dominate at greater distances.

Far-field strength decreases inversely with distance from the radiation source (inverse-square law), while near-field strength decreases more rapidly with distance from the radiation source. Part of the near-field decreases by the inverse-square law, the other by an inverse-cube law. The effect of near-field essentially vanishes a few wavelengths away from the radiation source. For example, when a BLE® communication interface is operating at 2.4 GHz, it will have a wavelength of 12.5 cm. This results in a negligible near-field region 520 for BLE®. Other communications technologies, such as NFMI radio communication technologies, have a near-field region 520 of roughly 1000 cm through inductive communications defined by energy instead of wavelength.

The various devices that are part of the insulin infusion system can all transmit and receive communications, and all are potentially mobile, and therefore can move inside and outside of the near-field region 520. Thus, depending on their location relative to a transmitting device that is part of the body area network, the various devices can potentially be part of the body area network. Depending on a particular device's proximity to the user 530, the device can be within either one or both of the above described coverage regions, but may also be outside any of the above described coverage regions. As described above, various devices that are typically worn on or implanted in the user's body, such as, the insulin infusion device, a continuous glucose monitoring device, a glucose sensor arrangement and possibly other devices (not illustrated in FIGS. 7 and 8) will normally be within the near-field communication coverage region 520 when they are worn on or implanted in the user's body. The near-field communication coverage region 520 corresponds to a wireless body area network coverage region that is associated with a particular user 530. Other devices, such as the user's mobile device 504 (or alternatively a monitor device, devices that are sources of contextual information, which may include, without limitation: data activity tracker devices; meal logging devices or apps; mood tracking devices or apps; and other devices, systems, and sources of input data, etc.) may be outside the near-field communication coverage region 520 depending on where the mobile device 504 is located relative to the user 530 at any particular time. For example, in FIG. 7, it is assumed that the user's mobile device 504 is located outside the near-field communication coverage region 520, but within the far-field coverage region 510, whereas in FIG. 8, the user's mobile device 504 is closer to the user and is located within the near-field communication coverage region 520 (and would still be within the far-field coverage region 510). As such, the options available for a particular device to communicate with other devices that are part of the body area network can vary depending on the device's proximity to other devices that are part of the body area network.

Figure 9:
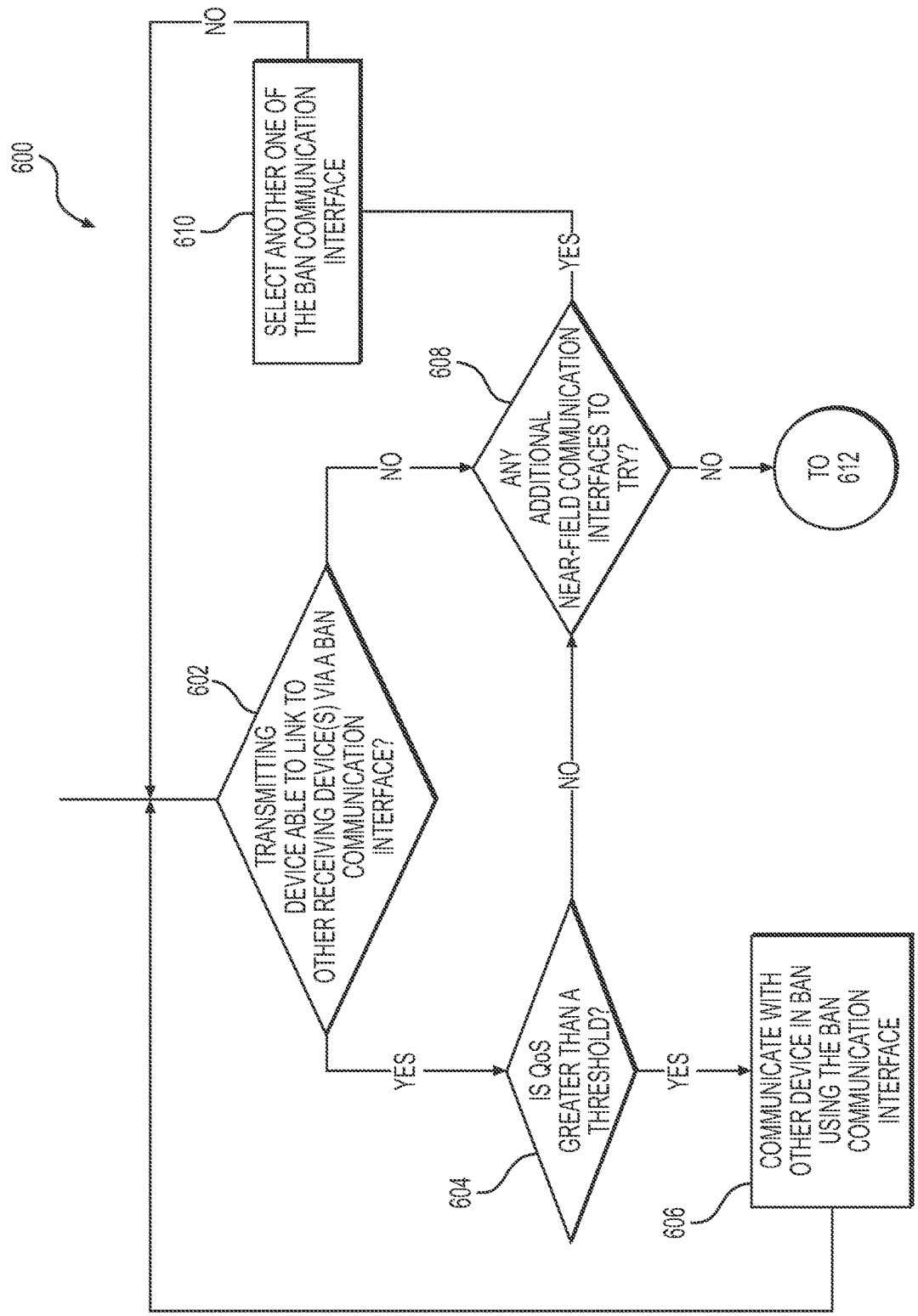
FIGS. 9 and 10 are collectively a flowchart that illustrates an exemplary embodiment of a method for controlling which communication interface is used by a device to communicate with another device that is part of a wireless body area network in accordance with the disclosed embodiments.
Figure 10:
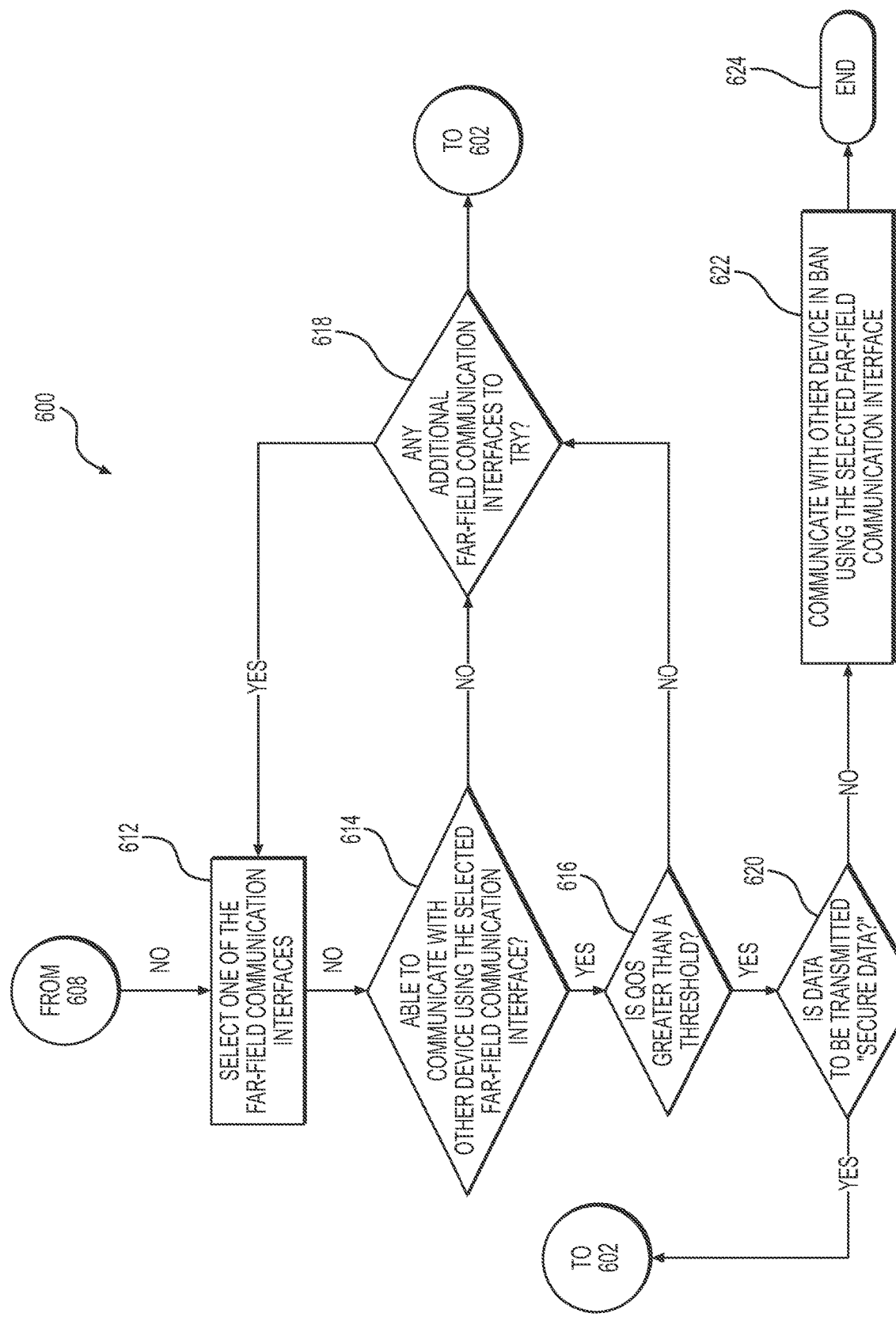

FIGS. 9 and 10 are collectively a flowchart that illustrates an exemplary embodiment of a method 600 for controlling which communication interface is used by a device to communicate with another device that is part of a wireless body area network in accordance with the disclosed embodiments. The method 600 can be used to control communication among devices that can be part of a wireless body area network as a device moves into and/or out of the near-field coverage region of the body area network. An example is described with reference to FIGS. 9 and 10, where one device that is part of the system (e.g., the systems that are described with reference to FIGS. 1 and 2) is communicating with (or attempting to communicate with) another device that is part of the system. However, it should be appreciated that other instances of the method 600 can be applied to each of the other devices that the device is communicating with (or attempting to communicate with). In addition, although the example that is described with reference to FIGS. 9 and 10 describes a scenario where one device that is part of the system is communicating with (or attempting to communicate with) another device that is part of the system, it should be appreciated that the same methodology can be applied in scenarios where one device that is part of the system is communicating with (or attempting to communicate with) multiple devices that are part of the system. With reference to method 600, steps can be added, omitted, and/or performed simultaneously without departing from the scope of the appended claims. It should be appreciated that the method 600 may include any number of additional or alternative tasks, that the tasks shown in FIGS. 9 and 10 need not be performed in the illustrated order, and that the method 600 may be incorporated into a more comprehensive procedure or process having additional functionality not described in detail herein. Moreover, one or more of the tasks shown in FIGS. 9 and 10 could potentially be omitted from an embodiment of the method 600 as long as the intended overall functionality remains intact. It should also be understood that the illustrated method 600 can be stopped at any time. The method 600 is computer-implemented in that various tasks or steps that are performed in connection with the method 600 may be performed by software, hardware, firmware, or any combination thereof. For illustrative purposes, the following description of the method 600 may refer to elements mentioned above in connection with FIGS. 1-8. In certain embodiments, some or all steps of this process, and/or substantially equivalent steps, are performed by execution of processor-readable instructions stored or included on a processor-readable medium. For instance, in the description of FIGS. 9 and 10 that follows, the devices (or components) will be described as performing various acts, tasks or steps, but it should be appreciated that this refers to processing system(s) of these entities executing instructions to perform those various acts, tasks or steps.

The method 600 begins at 602, for example, when the controller 330 determines that the device is attempting to connect to and communicate with another device that is part of the system, or needs to transmit data to another device that is part of the system. At 602, the controller 330 determines whether the device is able to establish a communication link with the other device in the body area network using one of the body area network communication interfaces 322, 324, 326, 328.

When the controller 330 determines (at 602) that the device is able to establish a communication link with the other device using one of the body area network communication interfaces 322, 324, 326, 328, the method proceeds to 604. At 604, the controller 330 determines whether the quality of service over the communication link to the other device is greater than or equal to the threshold. In one embodiment, the controller 330 can make this determination by comparing any number or combination of different link quality metrics that have been measured to thresholds to determine whether or not the quality of service over that communication link is adequate.

When the controller 330 determines (at 604) that the quality of service over the communication link to the other device is greater than or equal to the threshold, the method 600 proceeds to 606, where the device communicates with the other device in the body area network using a particular one of the body area network communication interfaces 322, 324, 326, 328. Which one of the body area network communication interfaces 322, 324, 326, 328 is selected to be used can vary depending on the implementation.

The near-field communication region or bubble is small (e.g., 1 meter around the transmitting device in one implementation) and moveable along with the patient/user. The near-field communication region or bubble thus provides a well-defined cybersecurity attack region that is easily manageable, visually inspectable, and moveable with the user to make cybersecurity attack difficult. While transmissions within the near-field communication bubble normally carry a high expectation of secure transfer, in some implementations, a further layer of security can be provided prior to communicating "secure data" within the near-field bubble to provide another layer of protection in the event an eavesdropper device came within the near-field communication bubble. Although not illustrated in FIG. 6, in some implementations, cybersecurity secrets (such as public or private keys, digital signatures, and certificates, etc.) can be exchanged between devices to authenticate a new device to be paired, and to establish an encrypted channel that are within the near-field communication bubble. For example, an exchange of cybersecurity secrets (or equivalent) could be required to provide another hurdle for a potential eavesdropper. An exchange of cybersecurity secrets can include things such as a security key exchange protocol that allows an encrypted channel to be established, and other non-encryption or keys related secrets such as certificates, digital signatures, etc. depending on the specific implementation of the cybersecurity protocol.

For instance, the transmitting device and receiving devices would be required to successfully complete a security key exchange protocol before the transmitting device encrypts and transmits the data at each communication session. All of the devices that are intended to be part of the BAN could share a pre-established shared public and/or private keys known only by those devices (that is used to encrypt data), then even if an eavesdropper device was within the near-field communication bubble, the eavesdropper device could not process any data that is intercepted because they lack knowledge of the pre-established shared keys. Thus, once the cybersecurity secrets are exchanged, secure data (e.g., patient biometrics) can be encrypted by one device and then transmitted to the other and decrypted at another device. Furthermore, once a secure communication channel is established, the two communicating devices (e.g., infusion device and phone) can then be separated further, inside or outside the NF bubble, and exchange encryption data over the air securely.

Referring again to FIG. 9, when the controller 330 determines (at 602) that the device is unable to establish a communication link with the other device using one of the body area network communication interfaces 322, 324, 326, 328, the method 600 proceeds to 608. Similarly, when the controller 330 determines (at 604) that the quality of service over the communication link to the other device is less than the threshold, the method 600 proceeds to 608.

At 608, the controller 330 determines whether there are any additional near-field body area network communication interfaces 322, 324, 326, 328 to try (i.e., potentially use to communicate with the other device). When the controller 330 determines (at 608) that there are other body area network communication interfaces 322, 324, 326, 328 to try, the method 600 proceeds to 610, where the controller 330 selects another one of the near-field body area network communication interfaces 322, 324, 326, 328, and the method 600 then loops back to 602. When the controller 330 determines (at 608) that there are not any other body area network communication interfaces 322, 324, 326, 328 to potentially use, the method 600 proceeds to 612.

As shown in FIG. 10, at 612, the controller 330 selects one of the far-field communication interfaces 314, 316, 318, 320, and then proceeds to 614. At 614, the controller 330 determines whether the device is able to establish a communication link with the other device in the body area network using the selected far-field communication interface (the far-field communication interface that was selected at 612).

When the controller 330 determines (at 614) that the device is able to establish a communication link with the other device using the selected far-field communication interface, the method proceeds to 616. At 616, the controller 330 determines whether the quality of service over the communication link to the other device is greater than or equal to the threshold. In one embodiment, the controller 330 can make this determination by comparing any number or combination of different link quality metrics that have been measured to thresholds to determine whether or not the quality of service over that communication link is adequate.

When the controller 330 determines (at 616) that the quality of service over the communication link to the other device is greater than or equal to the threshold, the method 600 proceeds to 620. At 620, the controller 330 determines whether the security type of the data to be transmitted by the device is "secure data." As used herein, "secure data" can refer to information or data having a data type which indicates that a communication of that data is restricted such that it is communicated only to devices that are within the near-field region of the device that is transmitting that data. In other words, any data that has a secure data type can only be communicated when a transmitter of that data is communicating it to one or more other devices that are within a protected, ultra-secure zone/region (e.g., within a one meter radius of a transmitter of that secure data), which is referred to herein as a near-field region, or near-field communication region. This way, secure data cannot be intercepted by any device that is outside the near-field region and is protected by an enhanced level of security (e.g., beyond encryption). For instance, "secure data" can be communicated via a near-field communication interfaces to other devices within a near-field physical boundary such that data communicated within a communication bubble defined by near-field boundary are protected from being intercepted via eavesdropping.

Data that has a secure data type can be data that, if compromised, can be used to adversely affect a patient. For example, secure data can include data, such as, patient biometrics (e.g., blood glucose level), therapy data (e.g., insulin dosage, basal rate, bolus pattern, etc.), cybersecurity information (e.g., information relating to public or private key authentication, encryption, digital signatures, and other secret information, etc.), and other data that are communicated between a glucose sensor and an insulin infusion device. For instance, data concerning a tissue glucose level of a patient, if comprised, could be used to send improper tissue glucose levels to the insulin pump in an effort to overdose the patient with insulin.

Referring again to FIG. 6, when the controller 330 determines (at 620) that the security type of the data to be transmitted by the device to another device (e.g., body worn device) is secure data, the method 600 loops back to 602. In other words, when the data being communicated is secure data and cannot be communicated using one of the body area network communication interfaces 322, 324, 326, 328, the secure data will not be communicated until one of the body area network communication interfaces 322, 324, 326, 328 can be used to communicate that secure data (e.g., the data will not be communicated using one of the far-field communication interfaces because doing so would be a potential security risk).

When the controller 330 determines (at 620) that the security type of the data to be transmitted by the device is not secure, the method 600 proceeds to 622. At 622, the device communicates with other devices in the body area network using the far-field communication interface that was most recently selected at 612. Thus, when the controller 330 determines (at 620) that the data that is to be communicated by the device is not highly secure data, the controller 330 routes communications through the selected far-field communication interface so that the device communicates the data with other devices that are part of the body area network using the selected far-field communication interface. In other words, because the data is not highly secure, it can be communicated using the selected far-field communication interface because doing so would not be a potential security risk. For instance, less secure data can still be encrypted to offer a level of security, but can still be transmitted using a far-field communication interface because these other types of less secure data have lower security requirements (e.g., interception via eavesdroppers is not a concern). The method 600 then ends at 624.

When the controller 330 determines (at 614) that the device is unable to establish a communication link with the other device using the selected far-field communication interface, the method 600 proceeds to 618. Similarly, when the controller 330 determines (at 616) that the quality of service over the communication link to the other device is less than the threshold, the method 600 proceeds to 618. At 618, the controller 330 determines whether there are any additional far-field communication interfaces 314, 316, 318, 320 to try (i.e., potentially use to communicate with the other device). When the controller 330 determines (at 618) that there are other far-field communication interfaces 314, 316, 318, 320 to try, the method 600 loops back to 612, where the controller 330 selects another one of the far-field communication interfaces 314, 316, 318, 320, and the method 600 the proceeds to 614. When the controller 330 determines (at 618) that there are not any other far-field communication interfaces 314, 316, 318, 320 to potentially use, the method 600 loops back to 602.

Example Scenario

For example, in one non-limiting scenario, when the controller 330 determines that the client device 204 (e.g., patient's smartphone) is attempting to communicate with to an insulin infusion device 206 that is part of the system, or needs to transmit data to the insulin infusion device 206 that is part of the system, the controller 330 determines whether the client device 204 is able to establish a communication link with the insulin infusion device 206 in the body area network using one of the body area network communication interfaces 322, 324, 326, 328, such as the NFMI radio communication interface 322 (e.g., that the device is within a body area network).

When the controller 330 determines that the client device 204 can establish a communication link with the insulin infusion device 206 using the NFMI radio communication interface 322, the controller 330 determines whether the quality of service over the communication link to the insulin infusion device 206 is greater than or equal to the threshold. In one embodiment, the controller 330 can make this determination by comparing any number or combination of different link quality of service metrics that have been measured to thresholds to determine whether or not the quality of service over that communication link is adequate.

When the controller 330 determines that the quality of service over the communication link to the insulin infusion device 206 is greater than or equal to the threshold, the client device 204 communicates with the insulin infusion device 206 in the body area network using the NFMI radio communication interface 322. For example, the controller 330 routes communications through the NF communication interface 312 so that the device can communicate with other devices in the body area network using the NF communication interface 312.

When the controller 330 determines that the client device 204 is unable to establish a communication link with the insulin infusion device 206 using the NFMI radio communication interface 322, or when the controller 330 determines that the quality of service over the communication link to the insulin infusion device 206 is less than the threshold, the controller 330 determines whether there are any additional body area network communication interfaces 324, 326, 328 available to potentially use to communicate with the insulin infusion device 206. When the controller 330 determines that one of the other body area network communication interfaces 324, 326, 328 is available to potentially use to communicate with the insulin infusion device 206, the controller 330 selects that one of the body area network communication interfaces 322, 324, 326, 328, and determines whether the client device 204 is able to establish a communication link with the insulin infusion device 206, and determines whether the quality of service over the communication link to the insulin infusion device 206 is greater than or equal to the threshold, etc.

When the controller 330 determines that there are not any other body area network communication interfaces 324, 326, 328 to potentially use, the controller 330 selects one of the far-field communication interfaces 314, 316, 318, 320, such as the BLE® communication interface 314, and then determines whether the client device 204 is able to establish a communication link with the insulin infusion device 206 in the body area network using the selected BLE® communication interface 314.

When the controller 330 determines that the client device 204 is able to establish a communication link with the insulin infusion device 206 using the selected BLE® communication interface 314, the controller 330 determines whether the quality of service over the communication link to the insulin infusion device 206 is greater than or equal to the threshold, and if so, the controller 330 can determine whether the security type of the data to be transmitted by the client device 204 is secure. If the controller 330 determines that the client device is able to pair with the insulin infusion device using the BLE® communication interface 314 (e.g., that the device is within BLE® communication range), and then determines that QoS is adequate and that the security type of the data to be transmitted by the client device 204 is not secure, then the client device 204 routes communications through the BLE® communication interface 314 so that the client device communicates with the communicates with the insulin infusion device 206 using the BLE® communication interface 314.

On the other hand, when the controller 330 determines that the client device 204 is unable to establish a communication link with the insulin infusion device 206 using the selected BLE® communication interface 314, or determines that the quality of service over the communication link to the insulin infusion device 206 is less than the threshold, the controller 330 determines whether there are any other far-field communication interfaces 316, 318, 320 to potentially use to communicate with the insulin infusion device 206, and if so, the controller 330 selects another one of the far-field communication interfaces 316, 318, 320 and determines whether it can link to the insulin infusion device, whether the QoS is adequate, and whether the security type of the data meets is non-secure. If the controller 330 eventually finds another far-field communication interface 316, 318, 320 (e.g., a communication interface other than the BLE® communication interface 314) that meets all of the QoS and security requirements, the controller 330 can then route communications through that other far-field communication interface 316, 318, 320 to communicate with the insulin infusion device 206. When the controller 330 determines that there are not any other far-field communication interfaces 316, 318, 320 to potentially use, the controller waits until one of the one of the body area network communication interfaces 322, 324, 326, 328 becomes available and can establish a communication link with the insulin infusion device 206 that meets quality of service requirements.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

What is claimed is:

1. A method for controlling which communication interface of a plurality of communication interfaces is used for communication between a plurality of devices that are configurable to be part of a wireless body area network for a medical device system depending on their respective locations with respect to a first device, the method comprising:
when a communication link is established between the first device and a second device that is located in a coverage region of the wireless body area network using a first body area network communication interface: determining, at a controller, whether a quality of service over the communication link is greater than or equal to a first threshold; and
using the first body area network communication interface to communicate data from the first device to the second device via magnetic signals when the controller determines that the quality of service over the communication link is greater than or equal to the first threshold.

2. The method of claim 1, wherein the first device and the second device each comprise a plurality of body area network communication interfaces that are used to communicate via near-field communications using magnetic signals, and wherein the first body area network communication interface comprises:
a near-field magnetic induction (NFMI) radio communication interface;
a near-field electromagnetic induction (NFeMI) radio communication interface;
a near-field communication (NFC) interface; or
a high-frequency radio-frequency identification (RFID) communication interface.

3. The method of claim 1, further comprising:
determining, at the controller, whether the communication link between the first device and the second device is established using the first body area network communication interface;
when the communication link is not established between the first device and the second device using the first body area network communication interface or when the quality of service over the communication link is less than the first threshold:
determining, at the controller, whether there is a second body area network communication interface available to potentially use to communicate with the second device;
when the controller determines that the second body area network communication interface is available:
determining, at the controller, whether the communication link between the first device and the second device is established using the second body area network communication interface;
when the controller determines that the communication link with the second device is established using the second body area network communication interface: determining, at the controller, whether the quality of service over that communication link is greater than or equal to the first threshold; and
using the second body area network communication interface to communicate the data from the first device to the second device via magnetic signals when the controller determines that the quality of service over that communication link is greater than or equal to the first threshold.

4. The method of claim 3, further comprising:
when the controller determines that the second body area network communication interface is not available:
selecting, at the controller, a first far-field communication interface;
determining, at the controller, whether the communication link between the first device and the second device is established using the first far-field communication interface;
when the communication link is established between the first device and the second device using the first far-field communication interface: determining, at the controller, whether the quality of service over that communication link is greater than or equal to the first threshold; and
using the first far-field communication interface to communicate the data from the first device to the second device via electromagnetic signals when the controller determines that the quality of service over the communication link is greater than or equal to the first threshold.

5. The method of claim 1, further comprising:
when the controller determines that the second body area network communication interface is not available:
selecting, at the controller, a first far-field communication interface;
determining, at the controller, whether the communication link between the first device and the second device is established using the first far-field communication interface;
when the communication link is established between the first device and the second device using the first far-field communication interface:
determining, at the controller, whether the quality of service over that communication link is greater than or equal to the first threshold;
when the controller determines that the quality of service over the communication link is greater than or equal to the first threshold, determining, at the controller, whether data to be communicated by the first device is secure data; and
using the first far-field communication interface to communicate the data from the first device to the second device via electromagnetic signals when the controller determines that the data to be communicated by the first device is not secure data.

6. The method of claim 5, further comprising:
when the controller determines that the data to be communicated by the first device is secure data, waiting, at the controller, for a body area network communication interface to become available;
determining, at the controller, whether the communication link between the first device and the second device is established using the available body area network communication interface;
when the communication link is established between the first device and the second device using the available body area network communication interface: determining, at the controller whether a quality of service over that communication link is greater than or equal to the first threshold; and
using the available body area network communication interface to communicate data from the first device to the second device via magnetic signals when the controller determines that the quality of service over that communication link is greater than or equal to the first threshold.

7. The method of claim 5, further comprising:
when the communication link is not established between the first device and the second device using the first far-field communication interface or the quality of service over the communication link established with the second device using the first far-field communication interface is less than the first threshold, determining, at the controller, whether there are any additional far-field communication interfaces that are available to potentially use to communicate with the second device;
selecting a second far-field communication interface at the controller;
determining, at the controller, whether the communication link between the first device and the second device is established using the second far-field communication interface;
when the communication link is not established between the first device and the second device using the second far-field communication interface: determining, at the controller, whether the quality of service over that communication link is greater than or equal to the first threshold;
when the controller determines that the quality of service over the communication link is greater than or equal to the first threshold, determining, at the controller, whether data to be communicated by the first device is secure data; and
using the second far-field communication interface to communicate the data from the first device to the second device via electromagnetic signals when the controller determines that the data to be communicated by the first device is not secure data.

8. The method of claim 7, wherein the first device and the second device each comprise a plurality of far-field communication interfaces that are used to communicate via far-field communications using electromagnetic signals, and wherein the first far-field communication interface comprises:
a Bluetooth Low Energy® (BLE) communication interface;
a classical Bluetooth® (BT) communication interface; or
a Wireless Local Area Network (WLAN) communication interface.

9. The method of claim 1, wherein the medical device system is an insulin infusion system that comprises: an insulin infusion device configured to deliver insulin to a user, and wherein the first device is one of:
a mobile client device;
the insulin infusion device; and
a glucose sensor arrangement.

10. The method of claim 1, wherein the medical device system is an insulin infusion system that comprises: an insulin infusion device configured to deliver insulin to a user, and wherein the second device is one of:
a mobile client device;
the insulin infusion device; and
a glucose sensor arrangement.

11. A first device, comprising:
at least one processor device; and
a non-transitory processor-readable medium operatively associated with the at least one processor device, the processor-readable medium comprising executable instructions configurable to cause the at least one processor device to perform a method for controlling which communication interface of a plurality of communication interfaces is used for communication with a second device that is configurable to be part of a wireless body area network for a medical device system, wherein the first device and the second device are implemented as part of the medical device system, the method comprising:
when a communication link is established between the first device and a second device that is located in a coverage region of the wireless body area network using a first body area network communication interface: determining whether a quality of service over the communication link is greater than or equal to a first threshold; and
using the first body area network communication interface to communicate data from the first device to the second device via magnetic signals when the quality of service over the communication link is determined to be greater than or equal to the first threshold.

12. The first device of claim 11, wherein the first device and the second device are each exclusively one of: a mobile client device; an insulin infusion device configured to deliver insulin to a user; and a glucose sensor arrangement, wherein the first device and the second device each comprise:
a plurality of body area network communication interfaces that are used to communicate via near-field communications using magnetic signals, comprising: a near-field magnetic induction (NFMI) radio communication interface; a near-field electromagnetic induction (NFeMI) radio communication interface; a near-field communication (NFC) interface; or a high-frequency radio-frequency identification (RFID) communication interface; and
a plurality of far-field communication interfaces that are used to communicate via far-field communications using electromagnetic signals, comprising: a Bluetooth Low Energy® (BLE) communication interface; a classical Bluetooth® (BT) communication interface; or a Wireless Local Area Network (WLAN) communication interface.

13. The first device of claim 11, wherein the method further comprises:
determining whether the communication link between the first device and the second device is established using the first body area network communication interface;
when the communication link is not established between the first device and the second device using the first body area network communication interface or when the quality of service over the communication link is less than the first threshold:
determining whether a second body area network communication interface is available to potentially use to communicate with the second device;
when the second body area network communication interface is determined to be available:
determining whether the communication link between the first device and the second device is established using the second body area network communication interface;
determining, when the communication link between the first device and the second device is established using the second body area network communication interface, whether the quality of service over that communication link is greater than or equal to the first threshold; and
using the second body area network communication interface to communicate the data from the first device to the second device via magnetic signals when the quality of service over that communication link is greater than or equal to the first threshold.

14. The first device of claim 13, wherein the method further comprises:
when the second body area network communication interface is not available:
selecting a first far-field communication interface;
determining whether the communication link between the first device and the second device is established using the first far-field communication interface;
when the communication link is established between the first device and the second device using the first far-field communication interface:
determining whether the quality of service over that communication link is greater than or equal to the first threshold;
determining, when the quality of service over that communication link is determined to be greater than or equal to the first threshold, whether data to be communicated by the first device is secure data;
using the first far-field communication interface to communicate the data from the first device to the second device via electromagnetic signals when the data to be communicated by the first device is determined not to be secure data; and
waiting for a body area network communication interface to become available when the data to be communicated by the first device is secure data.

15. A wireless body area network for an insulin infusion system, comprising:
a plurality of devices that are configurable to be part of the wireless body area network depending on location, comprising: an insulin infusion device configured to deliver insulin to a user; a glucose sensor; and a mobile client device, wherein one of the plurality of devices is a first device and another one of the plurality of devices is a second device, the first device comprising:
a processor device that controls communication with the other devices that are configurable to be part of the wireless body area network depending on their respective locations with respect to the first device; and
a non-transitory processor-readable medium operatively associated with the processor device, the processor-readable medium comprising executable instructions configurable to cause the processor device to perform a method for controlling which communication interface of a plurality of communication interfaces is to be used for communication with the second device, the method comprising:
when a communication link is established between the first device and a second device that is located in a coverage region of the wireless body area network using a first body area network communication interface: determining whether a quality of service over the communication link is greater than or equal to a first threshold by comparing at least one link quality metric to the first threshold to determine whether the quality of service over that communication link is adequate; and
using the first body area network communication interface to communicate data from the first device to the second device via magnetic signals when the quality of service over the communication link is determined to be greater than or equal to the first threshold.

16. The wireless body area network of claim 15, wherein the first device and the second device each comprise:
a plurality of body area network communication interfaces that are used to communicate via near-field communications using magnetic signals, comprising: a near-field magnetic induction (NFMI) radio communication interface; a near-field electromagnetic induction (NFeMI) radio communication interface; a near-field communication (NFC) interface; or a high-frequency radio-frequency identification (RFID) communication interface.

17. The wireless body area network of claim 16, wherein the first device and the second device each further comprise:
a plurality of far-field communication interfaces that are used to communicate via far-field communications using electromagnetic signals, comprising: a Bluetooth Low Energy® (BLE) communication interface; a classical Bluetooth® (BT) communication interface; or a Wireless Local Area Network (WLAN) communication interface.

18. The wireless body area network of claim 15, wherein the method further comprises:
when the communication link is not established between the first device and the second device using the first body area network communication interface or when the quality of service over the communication link is less than the first threshold:
determining whether a second body area network communication interface is available to potentially use to communicate with the second device;
when the second body area network communication interface is determined to be available:
determining whether the communication link between the first device and the second device is established using the second body area network communication interface;
determining, when the communication link with the second device is established using the second body area network communication interface, whether the quality of service over that communication link is greater than or equal to the first threshold; and
using the second body area network communication interface to communicate the data from the first device to the second device via magnetic signals when the quality of service over that communication link is greater than or equal to the first threshold.

19. The wireless body area network of claim 17, wherein the method further comprises:
when the second body area network communication interface is determined to be not available:
selecting a first far-field communication interface;
determining whether the communication link between the first device and the second device is established using the first far-field communication interface;
when the communication link is established between the first device and the second device using the first far-field communication interface:
determining whether the quality of service over that communication link is greater than or equal to the first threshold;
determining, when the quality of service over that communication link is determined to be greater than or equal to the first threshold, whether data to be communicated by the first device is secure data; and
using the first far-field communication interface to communicate the data from the first device to the second device via electromagnetic signals when the data to be communicated by the first device is determined not to be secure data.

20. The wireless body area network of claim 19, wherein the method further comprises:
waiting for a body area network communication interface to become available when the data to be communicated by the first device is secure data.

* * * * *